United States Patent
Beavers et al.

(10) Patent No.: US 7,951,826 B2
(45) Date of Patent: May 31, 2011

(54) PYRROLIDINE DERIVATIVES AS HISTAMINE H3 RECEPTOR ANTAGONISTS

(75) Inventors: Lisa Selsam Beavers, Franklin, IN (US); Don Richard Finley, Greenwood, IN (US); Robert Alan Gadski, Indianapolis, IN (US); Philip Arthur Hipskind, New Palestine, IN (US); Cynthia Darshini Jesudason, Indianapolis, IN (US); Richard Todd Pickard, Noblesville, IN (US); Freddie Craig Stevens, Indianapolis, IN (US); Takako Takakuwa, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 871 days.

(21) Appl. No.: 11/908,501

(22) PCT Filed: Mar. 13, 2006

(86) PCT No.: PCT/US2006/008943
§ 371 (c)(1),
(2), (4) Date: Sep. 13, 2007

(87) PCT Pub. No.: WO2006/101808
PCT Pub. Date: Sep. 28, 2006

(65) Prior Publication Data
US 2008/0207732 A1    Aug. 28, 2008

Related U.S. Application Data

(60) Provisional application No. 60/662,686, filed on Mar. 17, 2005.

(51) Int. Cl.
*A61K 31/4439* (2006.01)
*A61K 31/4025* (2006.01)
*C07D 401/14* (2006.01)
*C07D 403/06* (2006.01)

(52) U.S. Cl. .............. 514/343; 514/422; 546/279.1; 548/518

(58) Field of Classification Search .......... 514/422; 548/518
See application file for complete search history.

(56) References Cited

U.S. PATENT DOCUMENTS

| 2008/0015235 A1 * | 1/2008 | Jesudason et al. | 514/364 |
| 2009/0118254 A1 * | 5/2009 | Beavers et al. | 514/210.18 |

FOREIGN PATENT DOCUMENTS

| EP | 0 494 010 | 7/1992 |
| WO | WO 96/38141 | 12/1996 |
| WO | WO 96/38142 | 12/1996 |
| WO | WO 02/076925 | 10/2002 |

* cited by examiner

*Primary Examiner* — Kamal A Saeed
*Assistant Examiner* — Kristin Bianchi
(74) *Attorney, Agent, or Firm* — Dan L. Wood

(57) ABSTRACT

The present invention discloses novel compounds of Formula (I) or pharmaceutically acceptable salts thereof which have histamine-H3 receptor antagonist or inverse agonist activity, as well as methods and intermediates for preparing such compounds. In another embodiment, the invention discloses pharmaceutical compositions comprising compounds of Formula (I) as well as methods of using them to treat obesity, cognitive deficiencies, narcolepsy, and other histamine H3 receptor-related diseases.

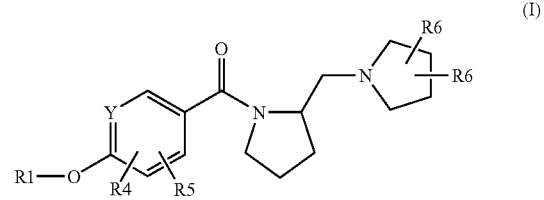

16 Claims, No Drawings

PYRROLIDINE DERIVATIVES AS HISTAMINE H3 RECEPTOR ANTAGONISTS

This is the national phase application, under 35 USC 371, for PCT/US2006/008943, filed Mar. 13, 2006, which claims the benefit, under 35 USC 119(e), of U.S. provisional application No. 60/662,686 filed Mar. 17, 2005.

The present invention relates to novel substituted phenyl-methanone-pyrrolidinyl-methyl-pyrrolidinyl compounds, and to the use of these compounds as pharmaceutical compositions, to pharmaceutical compositions comprising the compounds, to methods of treatment employing these compounds and compositions, and to intermediates and methods for making these compounds.

The histamine H3 receptor is relatively neuron specific and inhibits the release of a number of monoamines, including histamine. The histamine H3 receptor is a presynaptic autoreceptor and hetero-receptor located both in the central and the peripheral nervous system. The histamine H3 receptor regulates the release of histamine and other neurotransmitters, such as serotonin and acetylcholine. These are examples of histamine H3 receptor mediated responses. Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-regulated neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists, and antagonists could be important mediators of neuronal activity, and the activities of other cells that may express this receptor. Inverse agonism or selective antagonism of the histamine H3 receptor raises brain levels of histamine, and other monoamines, and inhibits activities such as food consumption while minimizing non-specific peripheral consequences. By this mechanism, they induce a prolonged wakefulness, improved cognitive function, reduction in food intake and normalization of vestibular reflexes. Accordingly, the histamine H3 receptor is an important target for new therapeutics in Alzheimer disease, mood and attention adjustments, cognitive deficiencies, obesity, dizziness, schizophrenia, epilepsy, sleeping disorders, narcolepsy and motion sickness.

Histamine mediates its activity via four receptor subtypes, H1R, H2R, H3R and a newly identified receptor designated GPRv53 [(Oda T., et al., J. Biol. Chem. 275 (47): 36781-6 (2000)], and alternative names for this receptor are PORT3 or H4R. Although relatively selective ligands have been developed for H1R, H2R and H3R, few specific ligands have been developed that can distinguish H3R from GPRv53. GPRv53 is a widely distributed receptor found at high levels in human leukocytes. Activation or inhibition of this receptor could result in undesirable side effects when targeting antagonism of the H3R receptor. The identification of the H4R receptor has fundamentally changed histamine biology and must be considered in the development of histamine H3 receptor antagonists.

Some histamine H3 receptor antagonists were created which resembled histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO96/38142. These imidazole-containing compounds have the disadvantage of poor blood-brain barrier penetration, interaction with cytochrome P-450 proteins, and hepatic and ocular toxicities. Recently other imidazole and non-imidazole ligands of the histamine H3 receptor have been described, such as those in WO2002076925. The compounds of the present invention differ in structure from the compounds described in the art.

There remains a need for improved treatments using alternative or improved pharmaceutical agents that act as histamine H3 receptor agonists, inverse agonists, or antagonists, to modulate H3 receptor activity, and treat the diseases that could benefit from H3 receptor modulation. The present invention provides such a contribution to the art based on the finding that a novel class of substituted phenyl-methanone-pyrrolidinyl-methyl-pyrrolidinyl compounds has a high affinity, selective, and potent activity at the histamine H3 receptor. The subject invention is distinct in the particular structures and their activities.

SUMMARY OF THE INVENTION

The present invention provides a compound structurally represented by Formula I:

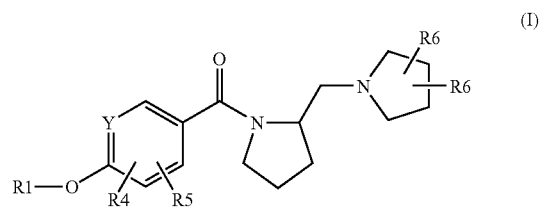

or a pharmaceutically acceptable salt thereof wherein:
Y independently represents carbon or nitrogen;
R1 is independently
—H,
provided that when R1 is H, and Y is carbon, and R5 is —H, then R4 is not fluorine attached to a position adjacent to the —OR1 substituent on the phenyl ring of the parent molecule; and further provided that when R1 is H, and Y is carbon, and R4 is —H, then R5 is not fluorine attached to a position adjacent to the —OR1 substituent on the phenyl ring of the parent molecule,
—($C_1$-$C_7$) alkyl (optionally substituted with 1 to 4 halogens, or wherein R1 is —$CH_3$, then optionally substituted with 1 to 3 halogens), provided that when Y is carbon, then R1 is not —$(CH_2)_3$—Cl,
—($C_3$-$C_8$) cycloalkyl (optionally substituted with 1 to 3 halogens),
—($C_1$-$C_7$) alkyl-O—R3, —($C_1$-$C_7$) alkyl-S(O)$_2$—($C_1$-$C_3$) alkyl,
—($C_1$-$C_7$) alkyl-C(O)—O—R3, —($C_1$-$C_7$) alkyl-S(O)$_2$-phenyl(R2)(R3)(R4),
—($C_1$-$C_7$) alkyl-S—($C_1$-$C_7$) alkyl, —($C_1$-$C_7$) alkyl-($C_3$-$C_8$) cycloalkyl,
—($C_1$-$C_7$) alkyl-O-phenyl(R2)(R3)(R4), —($C_2$-$C_7$) alkyl-phenyl(R2)(R3)(R4),
—($C_2$-$C_7$) alkenyl, —($C_3$-$C_8$) cycloalkenyl, —($C_2$-$C_7$) alkenyl-O—R3,
—($C_2$-$C_7$) alkenyl-S(O)$_2$—($C_1$-$C_3$) alkyl, —($C_2$-$C_7$) alkenyl-C(O)—O—R3,
—($C_2$-$C_7$) alkenyl-S(O)$_2$-phenyl(R2)(R3)(R4), —($C_2$-$C_7$) alkenyl-S—($C_1$-$C_7$) alkyl, —($C_2$-$C_7$) alkenyl-($C_3$-$C_8$) cycloalkyl, —($C_2$-$C_7$) alkenyl-O-phenyl(R2)(R3)(R4), —($C_2$-$C_7$) alkenyl-phenyl(R2)(R3)(R4), or -phenyl optionally substituted once or twice with R2, and independently optionally substituted once or twice with R3;

R2 is independently at each occurrence
—H, -halogen, —($C_1$-$C_7$) alkyl (optionally substituted with 1 to 3 halogens),
—C(O)R7, —C(O)OR7, —C(O)($C_3$-$C_8$)cycloalkyl,
—OCF$_3$, —OR7, —SR7, —SO$_2$R7, —SO$_2$CF$_3$, or —S(O)R7;

R3 is independently at each occurrence
—H, or —($C_1$-$C_4$) alkyl (optionally substituted with 1 to 3 halogens);

R4 and R5 are independently at each occurrence
—H, -halogen, —($C_1$-$C_3$) (alkyl optionally substituted with 1 to 3 halogens), or
—OR3, provided that when Y is nitrogen, then R4 or R5 are not attached to Y, R6 is independently at each occurrence
—H, -halogen, —CF$_3$, —($C_1$-$C_3$) alkyl (optionally substituted with 1 to 3 halogens), or
—OR3; and R7 is independently at each occurrence
—H, —($C_1$-$C_7$) alkyl, or —($C_2$-$C_7$) alkenyl (optionally substituted with 1 to 3 halogens).

The present invention provides compounds that show a selective and high affinity binding for the histamine H3 receptor, and thus the compounds are useful as histamine H3 receptor antagonists or inverse agonists. In another aspect, the present invention provides compounds that are useful as selective antagonists or inverse agonists of the histamine H3 receptor but have little or no binding affinity of GPRv53. In addition, the present invention provides a method for the treatment of a nervous system disorder, which comprises administering to a patient in need thereof an effective amount of a compound of formula I. The present invention further provides a method for the treatment of obesity or cognitive disorders, which comprises administering to a patient in need thereof an effective amount of a compound of formula I. In yet another aspect, the present invention provides pharmaceutical compositions comprising antagonists or inverse agonists of the histamine H3 receptor.

DETAILED DESCRIPTION OF THE INVENTION

In one embodiment, the present invention provides compounds of Formula I as described in detail above. While all of the compounds of the present invention are useful, certain of the compounds are particularly interesting and are preferred. The following listing sets out several groups of preferred compounds.

In a preferred embodiment, the present invention provides a compound structurally represented by Formula I or a pharmaceutically acceptable salt thereof wherein:

Y independently represents carbon;
R1 is independently
—H,
provided that when R1 is H, and Y is carbon, and R5 is —H, then R4 is not fluorine attached to a position adjacent to the —OR1 substituent on the phenyl ring of the parent molecule; and further provided that when R1 is H, and Y is carbon, and R4 is —H, then R5 is not fluorine attached to a position adjacent to the —OR1 substituent on the phenyl ring of the parent molecule, —($C_1$-$C_7$) alkyl (optionally substituted with 1 to 3 halogens), provided that R1 is not —(CH$_2$)$_3$—Cl,
—($C_3$-$C_8$) cycloalkyl (optionally substituted with 1 to 3 halogens),
—($C_1$-$C_7$) alkyl-O—R3, —($C_1$-$C_7$) alkyl-S(O)$_2$—($C_1$-$C_3$) alkyl,
—($C_1$-$C_7$) alkyl-C(O)—O—R3, —($C_1$-$C_7$) alkyl-S(O)$_2$-phenyl(R2)(R3)(R4),
—($C_1$-$C_7$) alkyl-S—($C_1$-$C_7$) alkyl, —($C_1$-$C_7$) alkyl-($C_3$-$C_8$) cycloalkyl,
—($C_1$-$C_7$) alkyl-O-phenyl(R2)(R3)(R4), —($C_2$-$C_7$) alkyl-phenyl(R2)(R3)(R4),
—($C_2$-$C_7$) alkenyl, —($C_3$-$C_8$) cycloalkenyl, —($C_2$-$C_7$) alkenyl-O—R3,
—($C_2$-$C_7$) alkenyl-S(O)$_2$—($C_1$-$C_3$) alkyl, —($C_2$-$C_7$) alkenyl-C(O)—O—R3,
—($C_2$-$C_7$) alkenyl-S(O)$_2$-phenyl(R2)(R3)(R4), —($C_2$-$C_7$) alkenyl-S—($C_1$-$C_7$) alkyl,
—($C_2$-$C_7$) alkenyl-($C_3$-$C_8$) cycloalkyl, —($C_2$-$C_7$) alkenyl-O-phenyl(R2)(R3)(R4),
—($C_2$-$C_7$) alkenyl-phenyl(R2)(R3)(R4), or -phenyl optionally substituted once or twice with R2, and independently optionally substituted once or twice with R3;

R2 is independently at each occurrence
—H, -halogen, —($C_1$-$C_7$) alkyl (optionally substituted with 1 to 3 halogens),
—C(O)R7, —C(O)OR7, —C(O)($C_3$-$C_8$)cycloalkyl,
—OCF$_3$, —OR7, —SR7, —SO$_2$R7, —SO$_2$CF$_3$, or —S(O)R7;

R3 is independently at each occurrence
—H, or —($C_1$-$C_4$) alkyl (optionally substituted with 1 to 3 halogens);

R4 and R5 are independently at each occurrence
—H, -halogen, —($C_1$-$C_3$) (alkyl optionally substituted with 1 to 3 halogens), or
—OR3;

R6 is independently at each occurrence
—H, -halogen, —CF$_3$, —($C_1$-$C_3$) alkyl (optionally substituted with 1 to 3 halogens), or
—OR3; and R7 is independently at each occurrence
—H, —($C_1$-$C_7$) alkyl, or —($C_2$-$C_7$) alkenyl.

In another preferred embodiment, the present invention provides a compound structurally represented by Formula I or a pharmaceutically acceptable salt thereof wherein:

Y independently represents nitrogen;
R1 is independently
—H,
—($C_1$-$C_7$) alkyl (optionally substituted with 1 to 3 halogens), provided that when Y is carbon, then R1 is not —(CH$_2$)$_3$—Cl,
—($C_3$-$C_8$) cycloalkyl (optionally substituted with 1 to 3 halogens),
—($C_1$-$C_7$) alkyl-O—R3, —($C_1$-$C_7$) alkyl-S(O)$_2$—($C_1$-$C_3$) alkyl,
—($C_1$-$C_7$) alkyl-C(O)—O—R3, —($C_1$-$C_7$) alkyl-S(O)$_2$-phenyl(R2)(R3)(R4),
—($C_1$-$C_7$) alkyl-S—($C_1$-$C_7$) alkyl, —($C_1$-$C_7$) alkyl-($C_3$-$C_8$) cycloalkyl,
—($C_1$-$C_7$) alkyl-O-phenyl(R2)(R3)(R4), —($C_2$-$C_7$) alkyl-phenyl(R2)(R3)(R4),
—($C_2$-$C_7$) alkenyl, —($C_3$-$C_8$) cycloalkenyl, —($C_2$-$C_7$) alkenyl-O—R3,
—($C_2$-$C_7$) alkenyl-S(O)$_2$—($C_1$-$C_3$) alkyl, —($C_2$-$C_7$) alkenyl-C(O)—O—R3, —($C_2$-$C_7$) alkenyl-S(O)$_2$-phenyl(R2)(R3)(R4), —($C_2$-$C_7$) alkenyl-S—($C_1$-$C_7$) alkyl, —($C_2$-$C_7$) alkenyl-($C_3$-$C_8$) cycloalkyl, —($C_2$-$C_7$) alkenyl-O-phenyl(R2)(R3)(R4), —($C_2$-$C_7$) alkenyl-phenyl(R2)(R3)(R4), or -phenyl optionally substituted once or twice with R2, and independently optionally substituted once or twice with R3;

R2 is independently at each occurrence
—H, -halogen, —($C_1$-$C_7$) alkyl (optionally substituted with 1 to 3 halogens),
—C(O)R7, —C(O)OR7, —C(O)($C_3$-$C_8$)cycloalkyl, —OCF$_3$, —OR7, —SR7, —SO$_2$R7, —SO$_2$CF$_3$, or —S(O)R7;

R3 is independently at each occurrence
—H, or —($C_1$-$C_4$) alkyl (optionally substituted with 1 to 3 halogens);

R4 and R5 are independently at each occurrence
—H, -halogen, —($C_1$-$C_3$) (alkyl optionally substituted with 1 to 3 halogens), or
—OR3, provided that when Y is nitrogen, then R4 or R5 are not attached to Y;

R6 is independently at each occurrence
—H, -halogen, —CF$_3$, —($C_1$-$C_3$) alkyl (optionally substituted with 1 to 3 halogens), or
—OR3; and R7 is independently at each occurrence
—H, —($C_1$-$C_7$) alkyl, or —($C_2$-$C_7$) alkenyl.

In another preferred embodiment, the present invention provides a compound structurally represented by Formula I or a pharmaceutically acceptable salt thereof wherein:

Y independently represents carbon or nitrogen;

R1 is independently
—($C_1$-$C_7$) alkyl (optionally substituted with 1 to 3 halogens), provided that when Y is carbon, then R1 is not —(CH$_2$)$_3$—Cl,
—($C_3$-$C_8$) cycloalkyl (optionally substituted with 1 to 3 halogens),
—($C_1$-$C_7$) alkyl-O—R3, —($C_1$-$C_7$) alkyl-S(O)$_2$—($C_1$-$C_3$) alkyl,
—($C_1$-$C_7$) alkyl-C(O)—O—R3, —($C_1$-$C_7$) alkyl-S(O)$_2$-phenyl(R2)(R3)(R4),
—($C_1$-$C_7$) alkyl-S—($C_1$-$C_7$) alkyl, —($C_1$-$C_7$) alkyl-($C_3$-$C_8$) cycloalkyl,
—($C_1$-$C_7$) alkyl-O-phenyl(R2)(R3)(R4), —($C_2$-$C_7$) alkyl-phenyl(R2)(R3)(R4),
—($C_2$-$C_7$) alkenyl, —($C_3$-$C_8$) cycloalkenyl, —($C_2$-$C_7$) alkenyl-O—R3,
—($C_2$-$C_7$) alkenyl-S(O)$_2$—($C_1$-$C_3$) alkyl, —($C_2$-$C_7$) alkenyl-C(O)—O—R3,
—($C_2$-$C_7$) alkenyl-S(O)$_2$-phenyl(R2)(R3)(R4), —($C_2$-$C_7$) alkenyl-S—($C_1$-$C_7$) alkyl,
—($C_2$-$C_7$) alkenyl-($C_3$-$C_8$) cycloalkyl, —($C_2$-$C_7$) alkenyl-O-phenyl(R2)(R3)(R4),
—($C_2$-$C_7$) alkenyl-phenyl(R2)(R3)(R4), or -phenyl optionally substituted once or twice with R2, and independently optionally substituted once or twice with R3;

R2 is independently at each occurrence
—H, -halogen, —($C_1$-$C_7$) alkyl (optionally substituted with 1 to 3 halogens),
—C(O)R7, —C(O)OR7, —C(O)($C_3$-$C_8$)cycloalkyl, —OCF$_3$, —OR7, —SR7, —SO$_2$R7, —SO$_2$CF$_3$, or —S(O)R7;

R3 is independently at each occurrence
—H, or —($C_1$-$C_4$) alkyl (optionally substituted with 1 to 3 halogens);

R4 and R5 are independently at each occurrence
—H, or -halogen, provided that when Y is nitrogen, then R4 or R5 are not attached to Y;

R6 is independently at each occurrence
—H, or —CH$_3$; and

R7 is independently at each occurrence
—H, —($C_1$-$C_7$) alkyl, or —($C_2$-$C_7$) alkenyl.

In another preferred embodiment, the present invention provides a compound structurally represented by Formula I or a pharmaceutically acceptable salt thereof wherein:

Y independently represents carbon or nitrogen;

R1 is independently
—($C_3$-$C_8$) cycloalkyl (optionally substituted with 1 to 3 halogens),
—($C_1$-$C_7$) alkyl-O—R3, —($C_1$-$C_7$) alkyl-S(O)$_2$—($C_1$-$C_3$) alkyl,
—($C_1$-$C_7$) alkyl-C(O)—O—R3, —($C_1$-$C_7$) alkyl-S(O)$_2$-phenyl(R2)(R3)(R4),
—($C_1$-$C_7$) alkyl-S—($C_1$-$C_7$) alkyl, —($C_1$-$C_7$) alkyl-($C_3$-$C_8$) cycloalkyl,
—($C_1$-$C_7$) alkyl-O-phenyl(R2)(R3)(R4), —($C_2$-$C_7$) alkyl-phenyl(R2)(R3)(R4),
—($C_2$-$C_7$) alkenyl, —($C_3$-$C_8$) cycloalkenyl, —($C_2$-$C_7$) alkenyl-O—R3,
—($C_2$-$C_7$) alkenyl-S(O)$_2$—($C_1$-$C_3$) alkyl, —($C_2$-$C_7$) alkenyl-C(O)—O—R3,
—($C_2$-$C_7$) alkenyl-S(O)$_2$-phenyl(R2)(R3)(R4), —($C_2$-$C_7$) alkenyl-S—($C_1$-$C_7$) alkyl,
—($C_2$-$C_7$) alkenyl-($C_3$-$C_8$) cycloalkyl, —($C_2$-$C_7$) alkenyl-O-phenyl(R2)(R3)(R4),
—($C_2$-$C_7$) alkenyl-phenyl(R2)(R3)(R4), or -phenyl optionally substituted once or twice with R2, and independently optionally substituted once or twice with R3;

R2 is independently at each occurrence
—H, -halogen, —($C_1$-$C_7$) alkyl (optionally substituted with 1 to 3 halogens),
—C(O)R7, —C(O)OR7, —C(O)($C_3$-$C_8$)cycloalkyl, —OCF$_3$, —OR7, —SR7, —SO$_2$R7, —SO$_2$CF$_3$, or —S(O)R7;

R3 is independently at each occurrence
—H, or —($C_1$-$C_4$) alkyl (optionally substituted with 1 to 3 halogens);

R4 and R5 are independently at each occurrence
—H, or -halogen, provided that when Y is nitrogen, then R4 or R5 are not attached to Y;

R6 is independently at each occurrence
—H, or —CH$_3$; and

R7 is independently at each occurrence —H, —($C_1$-$C_7$) alkyl, or —($C_2$-$C_7$) alkenyl.

In another embodiment the invention provides a pharmaceutical composition comprising a compound of Formula (II),

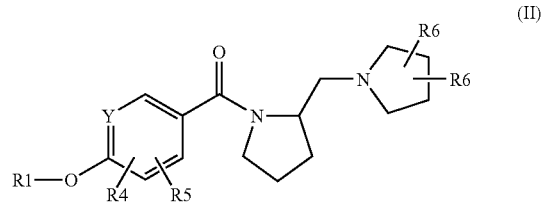

or a pharmaceutically acceptable salt thereof, and a pharmaceutically acceptable carrier, wherein:

Y independently represents carbon or nitrogen,
R1 is independently;
—H, —($C_1$-$C_7$) alkyl, —($C_3$-$C_8$) cycloalkyl, —($C_1$-$C_7$) alkyl-O—R3,
—($C_1$-$C_7$) alkyl-S(O)$_2$—($C_1$-$C_3$) alkyl, —($C_1$-$C_7$) alkyl-C(O)—O—R3,
—($C_1$-$C_7$) alkyl-S(O)$_2$-phenyl(R2)(R3)(R4), —($C_1$-$C_7$) alkyl-S—($C_1$-$C_7$) alkyl,
—($C_1$-$C_7$) alkyl-($C_3$-$C_8$) cycloalkyl, —($C_1$-$C_7$) alkyl-O-phenyl(R2)(R3)(R4),
—($C_2$-$C_7$) alkyl-phenyl(R2)(R3)(R4), —($C_2$-$C_7$) alkenyl, —($C_3$-$C_8$) cycloalkenyl,
—($C_2$-$C_7$) alkenyl-O—R3, —($C_2$-$C_7$) alkenyl-S(O)$_2$—($C_1$-$C_3$) alkyl,
—($C_2$-$C_7$) alkenyl-C(O)—O—R3, —($C_2$-$C_7$) alkenyl-S(O)$_2$-phenyl(R2)(R3)(R4),
—($C_2$-$C_7$) alkenyl-S—($C_1$-$C_7$) alkyl, —($C_2$-$C_7$) alkenyl-($C_3$-$C_8$) cycloalkyl,
—($C_2$-$C_7$) alkenyl-O-phenyl(R2)(R3)(R4), —($C_2$-$C_7$) alkenyl-phenyl(R2)(R3)(R4), or -phenyl optionally substituted once with R2, and independently optionally substituted once or twice with R3;
R2 is independently at each occurrence
—H, -halogen, —($C_1$-$C_7$) alkyl, —C(O)R7, —C(O)OR7, —C(O)($C_3$-$C_8$)cycloalkyl,
—OCF$_3$, —OR7, —SR7, —SO$_2$R7, —SO$_2$CF$_3$, or —S(O)R7;
R3 is independently at each occurrence
—H, or —($C_1$-$C_3$) alkyl;
R4 and R5 are independently at each occurrence
—H, -halogen, —($C_1$-$C_3$)alkyl, or —OR3,
provided that when Y is nitrogen, then R4 or R5 are not attached to Y;
R6 is independently at each occurrence
—H, -halogen, —CF$_3$, —($C_1$-$C_3$) alkyl, or —OR3;
R7 is independently at each occurrence
—H, —($C_1$-$C_7$) alkyl, or —($C_2$-$C_7$) alkenyl.

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference. Further, the invention provides a pharmaceutical composition comprising the compounds of the new embodiments created by the combinations of the embodiments described herein above with the narrowing preferences below, and a pharmaceutically acceptable carrier.

Preferably Y is carbon. Preferably Y is nitrogen.

Preferably R1 is —H, provided that when R1 is H, and Y is carbon, and R5 is —H, then R4 is not fluorine attached to a position adjacent to the —OR1 substituent on the phenyl ring of the parent molecule; and further provided that when R1 is H, and Y is carbon, and R4 is —H, then R5 is not fluorine attached to a position adjacent to the —OR1 substituent on the phenyl ring of the parent molecule. Preferably R1 is —($C_1$-$C_7$) alkyl (optionally substituted with 1 to 4 halogens, or wherein R1 is —CH$_3$, then optionally substituted with 1 to 3 halogens), provided that when Y is carbon, then R1 is not —(CH$_2$)$_3$—Cl. Preferably R1 is —($C_3$-$C_8$) cycloalkyl (optionally substituted with 1 to 3 halogens), —($C_1$-$C_7$) alkyl-O—R3, —($C_1$-$C_7$) alkyl-S(O)$_2$—($C_1$-$C_3$) alkyl, —($C_1$-$C_7$) alkyl-C(O)—O—R3, —($C_1$-$C_7$) alkyl-S(O)$_2$-phenyl(R2)(R3)(R4), —($C_1$-$C_7$) alkyl-S—($C_1$-$C_7$) alkyl, or —($C_1$-$C_7$) alkyl-($C_3$-$C_8$) cycloalkyl. Preferably R1 is —($C_1$-$C_7$) alkyl-O-phenyl(R2)(R3)(R4),
—($C_2$-$C_7$) alkenyl-S(O)$_2$-phenyl(R2)(R3)(R4), —($C_2$-$C_7$) alkenyl-O-phenyl(R2)(R3)(R4), —($C_2$-$C_7$) alkenyl-phenyl(R2)(R3)(R4), -phenyl optionally substituted once or twice with R2, and independently optionally substituted once or twice with R3,
or —($C_2$-$C_7$) alkyl-phenyl(R2)(R3)(R4). Preferably R1 is —($C_2$-$C_7$) alkenyl,
—($C_3$-$C_8$) cycloalkenyl, —($C_2$-$C_7$) alkenyl-O—R3, —($C_2$-$C_7$) alkenyl-S(O)$_2$—($C_1$-$C_3$) alkyl,
—($C_2$-$C_7$) alkenyl-C(O)—O—R3, —($C_2$-$C_7$) alkenyl-S—($C_1$-$C_7$) alkyl, or
—($C_2$-$C_7$) alkenyl-($C_3$-$C_8$) cycloalkyl.

Preferably R2 is independently at each occurrence —H. Preferably R2 is independently at each occurrence —H or halogen. Preferably R2 is independently at each occurrence -halogen, —($C_1$-$C_7$) alkyl (optionally substituted with 1 to 3 halogens), —C(O)R7, —C(O)OR7, —C(O)($C_3$-$C_8$)cycloalkyl, —OCF$_3$, —OR7, —SR7, —SO$_2$R7, —SO$_2$CF$_3$, or —S(O)R7.

Preferably R3 is independently at each occurrence —H. Preferably R3 is independently at each occurrence —($C_1$-$C_4$) alkyl (optionally substituted with 1 to 3 halogens).

Preferably R4 and R5 are independently at each occurrence —H. Preferably R4 and R5 are independently at each occurrence —H or -halogen. Preferably R4 and R5 are independently at each occurrence -halogen or —($C_1$-$C_3$) (alkyl optionally substituted with 1 to 3 halogens). Preferably R4 is hydrogen and R5 is -halogen.

Preferably R6 is independently at each occurrence —H. Preferably R6 is independently at each occurrence —H or —($C_1$-$C_3$) alkyl (optionally substituted with 1 to 3 halogens). Preferably R6 is independently at each occurrence —H or —CH$_3$ (optionally substituted with 1 to 3 halogens). Preferably one occurrence of R6 is —H and the second occurrence of R6 is —CH$_3$ (optionally substituted with 1 to 3 halogens). Preferably one occurrence of R6 is —H and the second occurrence of R6 is —CH$_3$.

Preferably R7 is independently at each occurrence —H. Preferably R7 is independently at each occurrence —($C_1$-$C_4$) alkyl. Preferably R7 is independently at each occurrence —($C_2$-$C_7$) alkenyl.

In another embodiment the present invention provides a compound structurally represented by Formula I or a pharmaceutically acceptable salt thereof, wherein:
Y independently represents carbon or nitrogen,
R1 is independently;
—H,
provided that when R1 is H, and Y is carbon, and R5 is —H, then R4 is not fluorine attached to a position adjacent to the —OR1 substituent on the phenyl ring of the parent molecule; and further provided that when R1 is H, and Y is carbon, and R4 is —H, then R5 is not fluorine attached to a position adjacent to the —OR1 substituent on the phenyl ring of the parent molecule,
—($C_1$-$C_7$) alkyl, provided that when Y is carbon, then R1 is not —(CH$_2$)$_3$—Cl,
—($C_3$-$C_8$) cycloalkyl, —($C_1$-$C_7$) alkyl-O—R3, —($C_1$-$C_7$) alkyl-S(O)$_2$—($C_1$-$C_3$) alkyl,
—($C_1$-$C_7$) alkyl-C(O)—O—R3, —($C_1$-$C_7$) alkyl-S(O)$_2$-phenyl(R2)(R3)(R4),
—($C_1$-$C_7$) alkyl-S—($C_1$-$C_7$) alkyl, —($C_1$-$C_7$) alkyl-($C_3$-$C_8$) cycloalkyl,
—($C_1$-$C_7$) alkyl-O-phenyl(R2)(R3)(R4), —($C_2$-$C_7$) alkyl-phenyl(R2)(R3)(R4),
—($C_2$-$C_7$) alkenyl, —($C_3$-$C_8$) cycloalkenyl, —($C_2$-$C_7$) alkenyl-O—R3, —(C$_2$-C$_7$) alkenyl-S(O)$_2$—(C$_1$-C$_3$) alkyl, —(C$_2$-C$_7$) alkenyl-C(O)—O—R3,
—(C$_2$-C$_7$) alkenyl-S(O)$_2$-phenyl(R2)(R3)(R4), —(C$_2$-C$_7$) alkenyl-S—(C$_1$-C$_7$) alkyl,
—(C$_2$-C$_7$) alkenyl-(C$_3$-C$_8$) cycloalkyl, —(C$_2$-C$_7$) alkenyl-O-phenyl(R2)(R3)(R4),
—(C$_2$-C$_7$) alkenyl-phenyl(R2)(R3)(R4), or -phenyl optionally substituted once or twice with R2, and independently optionally substituted once or twice with R3, R2 is independently at each occurrence
—H, -halogen, —(C$_1$-C$_7$) alkyl, —C(O)R7, —C(O)OR7, —C(O)(C$_3$-C$_8$)cycloalkyl,
—OCF$_3$, —OR7, —SR7, —SO$_2$R7, —SO$_2$CF$_3$, or —S(O)R7, R3 is independently at each occurrence;
—H, or —(C$_1$-C$_3$) alkyl, R4 and R5 are independently at each occurrence
—H, -halogen, —(C$_1$-C$_3$) alkyl, or —OR3,
provided that when Y is nitrogen, then R4 or R5 are not attached to Y, R6 is independently at each occurrence
—H, -halogen, —CF$_3$, —(C$_1$-C$_3$) alkyl, or —OR3, R7 is independently at each occurrence
—H, —(C$_1$-C$_7$) alkyl, or —(C$_2$-C$_7$) alkenyl.

The following listing sets out several groups of preferred compounds. It will be understood that each of the listings may be combined with other listings to create additional groups of preferred embodiments. Other embodiments are, 1. wherein Y is carbon,
2. wherein Y is nitrogen,
3. wherein R1 is —(C$_3$-C$_8$) cycloalkyl, —(C$_1$-C$_7$) alkyl-O—R3, —(C$_1$-C$_7$) alkyl-S(O)$_2$—(C$_1$-C$_3$) alkyl, —(C$_1$-C$_7$) alkyl-C(O)—O—R3, —(C$_1$-C$_7$) alkyl-S—(C$_1$-C$_7$) alkyl, —(C$_1$-C$_7$) alkyl-(C$_3$-C$_8$) cycloalkyl, or —(C$_1$-C$_7$) alkyl, provided that when Y is carbon, then R1 is not —(CH$_2$)$_3$—Cl,
4. wherein R1 is —(C$_1$-C$_7$) alkyl-O-phenyl(R2)(R3)(R4), —(C$_2$-C$_7$) alkyl-phenyl(R2)(R3)(R4), or —(C$_1$-C$_7$) alkyl-S(O)$_2$-phenyl(R2)(R3)(R4),
5. wherein R1 is —(C$_2$-C$_7$) alkenyl, —(C$_3$-C$_8$) cycloalkenyl, —(C$_2$-C$_7$) alkenyl-O—R3, —(C$_2$-C$_7$) alkenyl-S(O)$_2$—(C$_1$-C$_3$) alkyl, —(C$_2$-C$_7$) alkenyl-C(O)—O—R3, —(C$_2$-C$_7$) alkenyl-S—(C$_1$-C$_7$) alkyl, or —(C$_2$-C$_7$) alkenyl-(C$_3$-C$_8$) cycloalkyl,
6. wherein R1 is —(C$_2$-C$_7$) alkenyl-O-phenyl(R2)(R3)(R4), —(C$_2$-C$_7$) alkenyl-phenyl(R2)(R3)(R4), or —(C$_2$-C$_7$) alkenyl-S(O)$_2$-phenyl(R2)(R3)(R4),
7. wherein R1 is -phenyl optionally substituted once or twice with R2, and independently optionally substituted once or twice with R3,
8. wherein R1 is -phenyl optionally substituted once with R2, and twice with R3,
9. wherein R2 is —H, -halogen, —(C$_1$-C$_7$) alkyl, —C(O)R7, —C(O)OR7, —C(O)(C$_3$-C$_8$)cycloalkyl, —OCF$_3$, —OR7, —SR7, —SO$_2$R7, —SO$_2$CF$_3$, or —S(O)R7,
10. wherein R2 is -halogen, —(C$_1$-C$_7$) alkyl, —C(O)R7, —C(O)OR7, —OCF$_3$, —OR7, —SR7, —SO$_2$R7, —SO$_2$CF$_3$, or —S(O)R7,
11. wherein R2 is —SO$_2$R7, —SO$_2$CF$_3$, or —S(O)R7,
12. wherein R3 is —H, or —(C$_1$-C$_3$) alkyl,
13. wherein R3 is —(C$_1$-C$_3$) alkyl,
14. wherein R4 is halogen,
15. wherein R4 is halogen and R5 is halogen,
16. wherein one independent occurrence of R6 is —(C$_1$-C$_3$) alkyl,
17. wherein one independent occurrence of R6 is —CH$_3$,
18. A pharmaceutical composition comprising a compound of Formula (II),

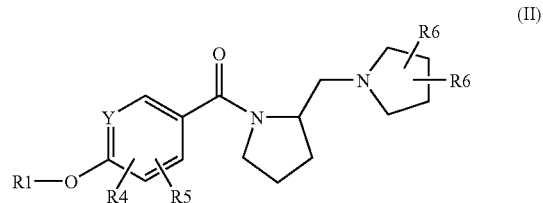

or a pharmaceutically acceptable salt thereof, and a pharmaceutically acceptable carrier, wherein:

Y independently represents carbon or nitrogen,

R1 is independently;
—H, —(C$_1$-C$_7$) alkyl, —(C$_3$-C$_8$) cycloalkyl, —(C$_1$-C$_7$) alkyl-O—R3,
—(C$_1$-C$_7$) alkyl-S(O)$_2$— (C$_1$-C$_3$) alkyl, —(C$_1$-C$_7$) alkyl-C(O)—O—R3,
—(C$_1$-C$_7$) alkyl-S(O)$_2$-phenyl(R2)(R3)(R4), —(C$_1$-C$_7$) alkyl-S—(C$_1$-C$_7$) alkyl,
—(C$_1$-C$_7$) alkyl-(C$_3$-C$_8$) cycloalkyl, —(C$_1$-C$_7$) alkyl-O-phenyl(R2)(R3)(R4),
—(C$_2$-C$_7$) alkyl-phenyl(R2)(R3)(R4), —(C$_2$-C$_7$) alkenyl, —(C$_3$-C$_8$) cycloalkenyl,
—(C$_2$-C$_7$) alkenyl-O—R3, —(C$_2$-C$_7$) alkenyl-S(O)$_2$—(C$_1$-C$_3$) alkyl,
—(C$_2$-C$_7$) alkenyl-C(O)—O—R3, —(C$_2$-C$_7$) alkenyl-S(O)$_2$-phenyl(R2)(R3)(R4),
—(C$_2$-C$_7$) alkenyl-S—(C$_1$-C$_7$) alkyl, —(C$_2$-C$_7$) alkenyl-(C$_3$-C$_8$) cycloalkyl,
—(C$_2$-C$_7$) alkenyl-O-phenyl(R2)(R3)(R4), —(C$_2$-C$_7$) alkenyl-phenyl(R2)(R3)(R4),
or -phenyl optionally substituted once with R2, and independently optionally substituted once or twice with R3, R2 is independently at each occurrence
—H, -halogen, —(C$_1$-C$_7$) alkyl, —C(O)R7, —C(O)OR7, —C(O)(C$_3$-C$_8$)cycloalkyl,
—OCF$_3$, —OR7, —SR7, —SO$_2$R7, —SO$_2$CF$_3$, or —S(O)R7, R3 is independently at each occurrence;
—H, or —(C$_1$-C$_3$) alkyl, R4 and R5 are independently at each occurrence
—H, -halogen, —(C$_1$-C$_3$)alkyl, or —OR3,
provided that when Y is nitrogen, then R4 or R5 are not attached to Y, R6 is independently at each occurrence
—H, -halogen, —CF$_3$, —(C$_1$-C$_3$) alkyl, or —OR3, R7 is independently at each occurrence
—H, —(C$_1$-C$_7$) alkyl, or —(C$_2$-C$_7$) alkenyl.

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R.

The term "H3R" means the histamine H3 receptor that inhibits the release of a number of monoamines, including histamine.

The term "H1R" means the histamine H1 receptor subtype.
The term "H2R" means the histamine H2 receptor subtype.
The term "H3R antagonists" is defined as a compound with the ability to block forskolin-stimulated cAMP production in response to agonist R-(−)α methylhistamine. The term "H3R inverse agonist" is defined as a compound with the ability to inhibit the constitutive activity of H3R. "Selective H3R antagonists or inverse agonists" means a compound of the present invention having a greater affinity for H3 histamine receptor than for GPRv53 histamine receptor.

In the general formulae of the present document, the general chemical terms have their usual meanings. For example;

The terms "($C_1$-$C_4$) alkyl", "($C_1$-$C_7$) alkyl", and "($C_2$-$C_7$) alkyl" mean hydrocarbon chains of the indicated number of carbon atoms, such as methyl, ethyl, propyl, butyl, pentyl, hexyl, heptyl, and the like, and branched or isomeric forms thereof, and as herein defined optionally may be substituted with up to four halogens.

"($C_3$-$C_8$) cycloalkyl" means a ring of the indicated number of carbon atoms, with three to eight carbon atoms, such as cyclopropyl, cyclobutyl, cyclopentyl and cyclohexyl, cycloheptyl, and the like, and as herein defined optionally may be substituted with up to four halogens.

"($C_2$-$C_7$) alkenyl" means hydrocarbon chains of the indicated number of carbon atoms, of either a straight or branched configuration, having at least one carbon-carbon double bond which may occur at any point along the chain, such as ethenyl, propenyl, butenyl, pentenyl, vinyl, alkyl, 2-butenyl and the like, and may be optionally substituted with up to four halogens.

The term "($C_3$-$C_8$) cycloalkenyl" refers to a partially saturated carbocycle containing one or more rings of from 3 to 8 carbon atoms, optionally substituted with up to four halogens.

"Boc" or "BOC" refer to t-butyl carbamate. "HOBt" is 1-hydrobenzotriazole. "PS-Trisamine" is Tris-(2-aminoethyl)amine polystyrene. "PS-Carbodiimide" or "PS-CDI" is N-Cyclohexylcarbodiimide-N'-propyloxymethyl polystyrene. "PS-DIEA" is N,N-(Diisopropyl)aminomethylpolystyrene (1% inorganic antistatic agent). "PS-DMAP" is N-(methylpolystyrene)-4-(methylamino) pyridine.

"Halogen" or "halo" means fluoro, chloro, bromo, and iodo.

"Composition" means a pharmaceutical composition and is intended to encompass a pharmaceutical product comprising the active ingredient(s) of Formula I, or II, or X1 to X55, and the inert ingredient(s) that make up the carrier. Accordingly, the pharmaceutical compositions of the present invention encompass any composition made by admixing a compound of the present invention and a pharmaceutically acceptable carrier.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The terms "treatment", "treating", and "treat", as used herein, include their generally accepted meanings, i.e., preventing, prohibiting, restraining, alleviating, ameliorating, slowing, stopping, or reversing the progression or severity of a pathological condition, described herein, including the alleviation or relief of symptoms or complications, or the cure or elimination of the disease, disorder, or condition.

Due to their interaction with the histamine H3 receptor, the present compounds are useful in the treatment of a wide range of conditions and disorders in which an interaction with the histamine H3 receptor is beneficial. The present invention also provides a pharmaceutical composition which comprises a compound of Formula I or Formula II or a pharmaceutical salt thereof, and a pharmaceutically acceptable carrier, diluent, or excipient. The present invention further provides an antagonist or inverse agonist of Formula I or Formula II which is characterized by having little or no binding affinity for the histamine receptor GPRv53. The present invention further provides an antagonist or inverse agonist of Formulae I or II which is characterized by having greater affinity for the histamine H3 receptor as compared to the affinity for the histamine H1R, H2R, or H4R receptors. The uses and methods of this invention encompass a prophylactic and therapeutic administration of a compound of Formula I, or pharmaceutical composition which comprises a compound of Formula I or Formula II or a pharmaceutical salt thereof. In addition the embodiments of the present invention include the synthesis of the examples named herein by methods included herein, and supplemented by methods known in the art, to create positron emission topography (PET) ligands that bind to histamine H3 receptors and are useful for PET imaging.

Thus, the invention provides a compound of Formula I, or a pharmaceutical salt thereof, or a pharmaceutical composition which comprises a compound of Formula I or Formula II, or a pharmaceutical salt thereof, for use to prevent, treat and/or alleviate diseases or conditions, for example, of the central nervous system, the peripheral nervous system, the cardiovascular system, the pulmonary system, the gastrointestinal system and the endocrinological system, while reducing and or eliminating one or more of the unwanted side effects associated with the current treatments. Such diseases or conditions include those responsive to the modulation of histamine H3 receptors, such as nervous system disorders, which include but are not limited to obesity, eating disorders, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, as well as cardiovascular disorders such as acute myocardial infarction; cancer such as cutaneous carcinoma, medullary thyroid carcinoma and melanoma; respiratory disorders such as asthma; gastrointestinal disorders, inflammation, and septic shock, diabetes, type II diabetes, insulin resistance syndrome, metabolic syndrome, polycystic ovary syndrome, Syndrome X, and the like. In addition, the compounds of Formula I, or a pharmaceutical salts thereof, or a pharmaceutical composition which comprises a compound of Formula I or Formula II, or a pharmaceutical salt thereof, can be useful in the treatment or prevention of a disorder or disease in which modulation of histamine H3 receptor activity has a beneficial effect. In yet another aspect, the present invention provides compounds, pharmaceutical compositions, and methods useful in the treatment of nervous system and other disorders associated with histamine H3 receptor.

In addition, the present invention provides a compound of Formula I, or a pharmaceutical salt thereof, or a pharmaceutical composition which comprises a compound of Formulae I or II, or a pharmaceutical salt thereof, and a pharmaceutically acceptable carrier, diluent, or excipient; for use in inhibiting the histamine H3 receptor; for use in inhibiting a histamine H3 receptor mediated cellular response in a mammal; for use to increase the release of H3 receptor-regulated neurotransmitters in a mammal; for use in treating a disease arising from excessive histamine H3 receptor activity.

The present invention is further related to the use of a compound of Formula I, or a pharmaceutical salt thereof, or a pharmaceutical composition which comprises a compound of Formulae I or II, or a pharmaceutical salt thereof, and a pharmaceutically acceptable carrier, diluent, or excipient; for the manufacture of a medicament for inhibiting the histamine H3 receptor; for the manufacture of a medicament for inhibiting a histamine H3 receptor mediated cellular response in a mammal; for the manufacture of a medicament to increase the release of H3 receptor-regulated neurotransmitters in the brain of a mammal; for the manufacture of a medicament for treating a disease arising from excessive histamine H3 receptor activity; for the manufacture of a medicament for treating cognitive disorders in a mammal; and for the manufacture of a medicament for treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo.

In addition, the present invention provides; a method of treating conditions resulting from excessive histamine H3 receptor activity in a mammal; a method of inhibiting the histamine H3 receptor activity in a mammal; a method of inhibiting a histamine H3 receptor mediated cellular response in a mammal; a method to increase the release of H3 receptor-regulated neurotransmitters in the brain of a mammal; a method of treating cognitive disorders in a mammal; a method of treating nervous system disorders in a mammal including but not limited to obesity, cognitive disorders, attention and attention deficit disorders, memory processes, learning, dementia, Alzheimer's disease, attention-deficit hyperactivity disorder, Parkinson's disease, schizophrenia, depression, epilepsy, and seizures or convulsions; comprising administering to a mammal in need of such treatment a histamine H3 receptor-inhibiting amount of a compound of Formula I, or a pharmaceutically acceptable salt thereof, or a pharmaceutical composition which comprises a compound of Formulae I or II, or a pharmaceutical salt thereof, and a pharmaceutically acceptable carrier, diluent, or excipient.

The invention further provides a method of selectively increasing histamine levels in cells, or increasing histamine release by cells, by contacting the cells with an antagonist or inverse agonist of the histamine H3 receptor, the antagonist or inverse agonist being a compound of Formula I, or a pharmaceutical composition comprising a compound of Formulae I or II, or a pharmaceutical salt thereof, and a pharmaceutically acceptable carrier, diluent, or excipient. The present invention further provides a method of treating conditions resulting from excessive histamine H3 receptor activity in a mammal comprising administering to a mammal in need of such treatment a histamine H3 receptor inhibiting amount of a pharmaceutical composition which comprises a compound of Formulae I or II, or a pharmaceutical salt thereof, and a pharmaceutically acceptable carrier, diluent, or excipient. In addition, a compound of Formula I, or a pharmaceutical composition comprising a compound of Formulae I or II, or a pharmaceutical salt thereof, can be useful in the treatment or prevention of a disorder or disease in which modulation of histamine H3 receptor activity has a beneficial effect.

The invention includes tautomers, enantiomers and other stereoisomers of the compounds also. Thus, as one skilled in the art knows, certain aryls may exist in tautomeric forms. Such variations are contemplated to be within the scope of the invention. It will be understood that, as used herein, references to the compounds of Formula I or Formula II are meant to also include the pharmaceutical salts, its enantiomers and racemic mixtures thereof.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I or Formula II can be prepared by one of ordinary skill in the art utilizing well known techniques and processes, such as those disclosed by J. Jacques, et al., "*Enantiomers, Racemates, and Resolutions,*" John Wiley and Sons, Inc., 1981, and E. L. Eliel and S. H. Wilen, "*Stereochemistry of Organic Compounds,*" (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation " ▬ " refers to a bond that protrudes forward out of the plane of the page. The designation " ⦀⦀⦀⦀ " refers to a bond that protrudes backward out of the plane of the page. The designation " ~~ " refers to a bond wherein the stereochemistry is not defined.

In general, the term "pharmaceutical" when used as an adjective means substantially non-toxic to living organisms. For example, the term "pharmaceutical salt" as used herein, refers to salts of the compounds of Formula I or Formula II which are substantially non-toxic to living organisms. See, e.g., Berge, S. M, Bighley, L. D., and Monkhouse, D. C., "Pharmaceutical Salts," *J. Pharm. Sci.*, 66:1, 1977. Typical pharmaceutical salts include those salts prepared by reaction of the compounds of Formula I or Formula II with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I or Formula II prepared by reaction of a compound of Formula I or Formula II with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of Formula I or Formula II with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "base addition salt" refers to a salt of a compound of Formula I or Formula II prepared by reaction of a compound of Formula I or Formula II with a mineral or organic base. For exemplification of pharmaceutical base addition salts see, e.g., Berge, S. M, Bighley, L. D., and Monkhouse, D. C., *J. Pharm. Sci.*, 66:1, 1977. The present invention also contemplates pharmaceutical base addition salts of compounds of Formula I or Formula II. The skilled artisan would appreciate that some compounds of Formula I or Formula II may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I or Formula II.

The compounds of Formula I or Formula II, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I or Formula II may be obtained by stereospecific synthesis using optically pure starting materials or reagents of known configuration or through enantioselective synthesis.

The compounds of Formula I or Formula II can be prepared by one of ordinary skill in the art following a variety of procedures, some of which are illustrated in the procedures and schemes set forth below. The particular order of steps required to produce the compounds of Formula I or Formula II is dependent upon the particular compound to being synthesized, the starting compound, and the relative liability of the substituted moieties. The reagents or starting materials are readily identifiable to and available to one of skill in the art, and to the extent not commercially available, are readily synthesized by one of ordinary skill in the art following standard procedures commonly employed in the art, along with the various procedures and schemes set forth below.

The following Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "μL"

refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates (M+1) unless indicated otherwise. "MS (FD)" refers to field desorption mass spectrometry, "MS(IS)" refers to ion spray mass spectrometry, "MS(FIA)" refers to flow injection analysis mass spectrometry, "MS(FAB)" refers to fast atom bombardment mass spectrometry, "MS(EI)" refers to electron impact mass spectrometry, "MS(ES)" refers to electron spray mass spectrometry, "UV" refers to ultraviolet spectrometry, "$^1$H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature.

General Preparations

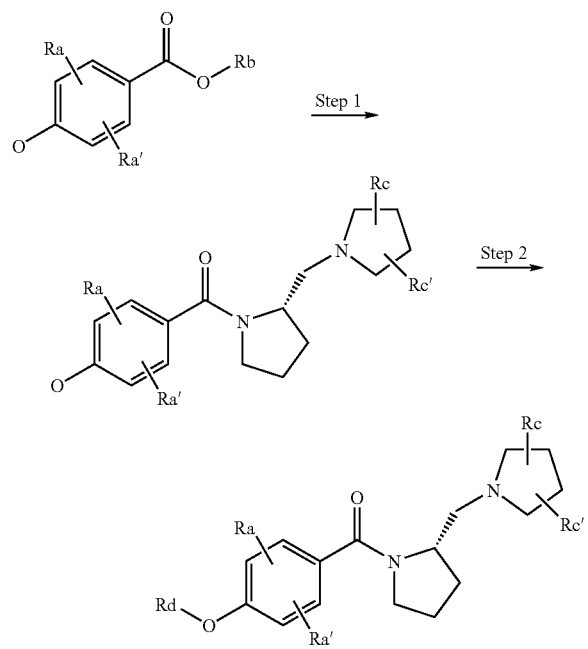

SCHEME A

In Scheme A, $R_a$ and $R_{a'}$ are each independently but not limited to F, Cl, $CF_3$, alkyl and can include disubstituted compounds; $R_b$ is H, or the corresponding carboxylic acids salts; $R_c$ and $R_{c'}$ are each independently but not limited to alkyl, hydroxy, and $R_d$ is an alkyl, branched alkyl group or cycloalkyl group which substituted with other functional groups not limited to sulfones, trifluoromethyl, halo, methoxy, ester, acid etc. In Scheme A, Step 1 aryl carboxylic acids or the lithium, sodium or potassium salt of the acid where $R_b$ can be H, Li, Na or K are converted to the corresponding amides using a number of different methods known in the literature. Some of these methods can be found described in a review of coupling reagents in peptide synthesis by Klausner & Bodansky, Synthesis, 1972, 9, 453-463.

For example, 4-hydroxybenzoic acid or the corresponding lithium or sodium salt is suspended a suitable organic solvent such as dichloromethane, DMF or mixtures thereof. A suitable amide coupling agent i.e. EDC, DCC, TBTU, etc., is added followed by HOBt, HATU, etc., at room temperature. Diisopropylethyl amine and suitable amine in this case, (S) (+)-1-(2-pyrrolidinylmethyl)pyrrolidine are added to the mixture. The mixture is stirred at room temperature for a period of 8-48 hours. The reaction is quenched by addition of water. The resulting mixture may be extracted, concentrated and purified according to techniques well known in the art.

Alternatively the corresponding acid chloride can be formed from the corresponding acid or salt thereof using thionyl chloride or oxalyl chloride and a few drops DMF, and treated with a suitable amine to give the desired amide.

In Scheme 1, Step 2 the phenols are converted to the ethers by alkylation with alkyl bromides, chlorides, iodides, mesylates, tosylate etc. with a suitable base such as $Cs_2CO_3$, $K_2CO_3$, or triethylamine etc. in a suitable solvent such as DMF, acetone, THF or $CH_2Cl_2$. The alkylation can carried out at room temperature or with heating.

For example, (4-hydroxy-phenyl)-(2-(S)-pyrrolidin-1-yl-methyl-pyrrolidin-1-yl)-methanone where $R_a$, $R_{a'}$=H and $Cs_2CO_3$ are suspended in DMF and 1-bromo-5-fluoropentane is added. The mixture is stirred at room temperature for 24-48 h. After an aqueous workup, the crude material may be purified by well known techniques.

Alternatively the ether can be formed by a Mitsunobu or related reaction using an alkyl alcohol and a coupling agent such as DEAD, DIAD etc. with triphenyl phosphine in a suitable solvent such as THF or $CH_2Cl_2$. The reaction is quenched with water, and the resulting mixture may be extracted, concentrated, and purified according to techniques well known in the art.

For example, (4-hydroxy-phenyl)-(2-(S)-pyrrolidin-1-yl-methyl-pyrrolidin-1-yl)-methanone where $R_a$, $R_{a'}$=H and 4-(methylthio)-1-butanol are treated with triphenyl phosphine and DEAD in THF. The mixture was stirred at room temperature for 12-48 hours. After an aqueous workup, the crude material may be purified by techniques well known in the art.

SCHEME B

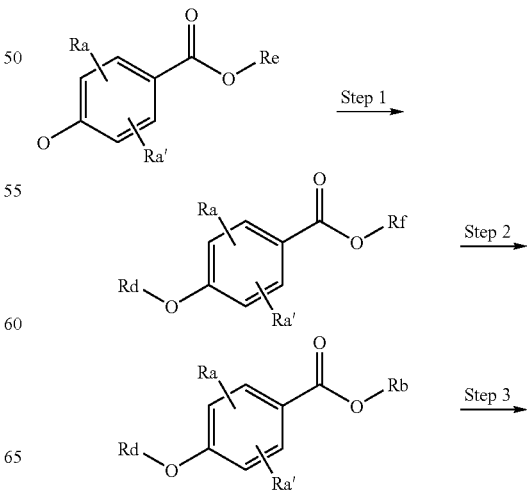

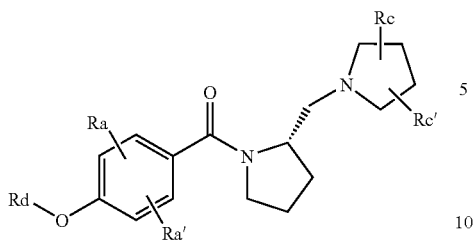

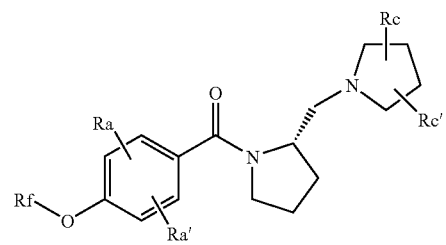

In Scheme B, $R_a$, $R_{a'}$, $R_b$, $R_c$, $R_{c'}$, and $R_d$ are as defined previously. $R_e$ can be Me, Et, Bz or butyl esters. In Scheme B (step 1), the carboxylic acid esters are alkylated by the methods described in Scheme A (step 2).

For example, 4-hydroxy-benzoic acid methyl ester, 1-bromo-3-fluoro-propane, and $K_2CO_3$ in acetone are heated at reflux for 18 h. The mixture is cooled to room temperature and filtered. The solvent is removed to provide the ether which can be purified by well known techniques or in some cases used without purification. In addition, the ether can be formed by a Mitsunobu or related reaction using an alkyl alcohol and a coupling agent such as DEAD, DIAD etc. with triphenyl phosphine in a suitable solvent such as THF or $CH_2Cl_2$. The reaction is quenched with water, and the resulting mixture may be extracted, concentrated, and purified according to techniques well known in the art.

For example, to a mixture of 4-hydroxy-benzoic acid methyl ester, 5-chloro-1-pentanol and triphenylphosphine in a suitable solvent such as THF is added DIAD. The mixture is stirred at room temperature for three days. The resulting mixture may be extracted, concentrated, and purified according to techniques well known in the art.

In Scheme B, Step 2, the resulting esters can be saponified using standard conditions to yield the corresponding carboxylic acids or the lithium, sodium or potassium salt of the acid where $R_b$ can be H, Li, Na or K. For example, to a mixture of 4-(3-fluoro-propoxy)-benzoic acid methyl ester in dioxane is added a solution of lithium hydroxide monohydrate in $H_2O$. The mixture is stirred at room temperature for 24-48 h. The solvent is removed in vacuo to provide the crude lithium salt which can be used without further purification.

In Scheme B, Step 3 the acids or the corresponding lithium, sodium or potassium salts (wherein $R_b$=H, Li, Na, K are converted to the pyrrolidinylmethylpyrrolidine amides by the methods described in Scheme A (step 1).

SCHEME C

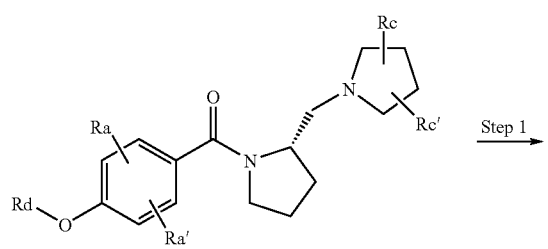

In Scheme C, $R_a$, $R_{a'}$, $R_c$, $R_{c'}$, and $R_d$ are as previously defined. $R_d$ contains any functional group that can be further modified to $R_f$ via alkylation, acylation, oxidation, reduction, sulfonylation etc. In Scheme C (step 1), wherein $R_f$=amino, $R_f$ can be converted to a sulfonamide using known sulfonylating conditions. For example, 5-[4-(2-Pyrrolidin-1-ylmethyl-pyrrolidine-1-carbonyl)-phenoxy]-pentanoic acid methyl ester is dissolved in a suitable solvent such as dioxane, or mixtures thereof in combination with 20 to 50% water by volume. To the reaction mixture is added lithium hydroxide monohydrate and the mixture stirred at ambient temperature for a period of 24 to 48 hours to yield 5-[4-(S)(+)-(2-Pyrrolidin-1-ylmethyl-pyrrolidine-1-carbonyl)-phenoxy]-pentanoic acid, lithium salt. The reaction is concentrated and purified according to techniques well known in the art.

SCHEME D

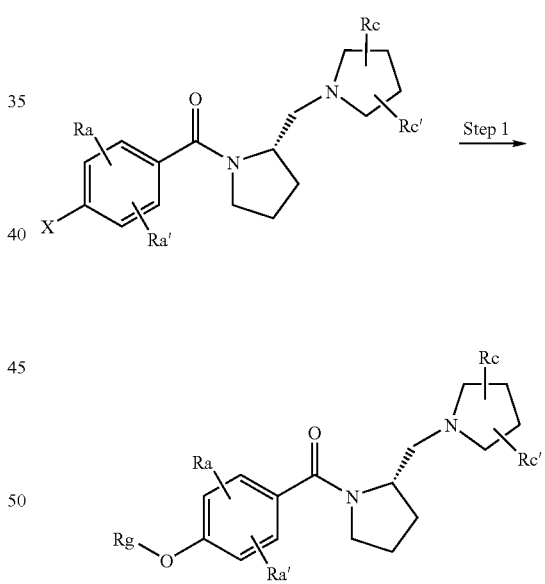

In Scheme D, $R_a$, $R_{a'}$, $R_c$, and $R_{c'}$, are as previously defined. $R_g$ is an aromatic group and X is a halogen. In Scheme D (step 1), the halide can be displaced by either a nucleophilic aromatic substitution or transition metal catalyzed reaction. For example, 4-bromo-phenyl)-(2-(S)-pyrrolidin-1-ylmethyl-pyrrolidin-yl)methanone is dissolved in a suitable solvent such as DMF. To the reaction mixture is added a suitable base such as potassium carbonate monohydrate and the heated at reflux for a period of 24 to 48 hours to yield [4-(4-Methanesulfonyl-phenoxy)-phenyl]-(2-(S)-pyrrolidin-1-ylmethyl-pyrrolidin-1-yl)-methanone. The reaction is concentrated and purified according to techniques well known in the art.

SCHEME E

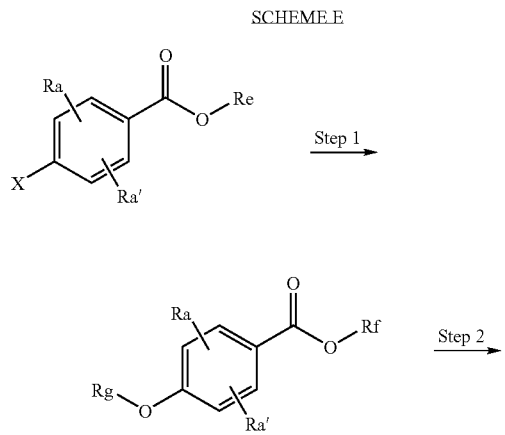

In Scheme D, $R_a$, $R_{a'}$, $R_c$, $R_{c'}$, $R_e$, $R_g$ and X are as previously defined. In Scheme D (step 1), the halide can be displaced by either a nucleophilic aromatic substitution or transition metal catalyzed reaction. For example, methyl-6-chloronicotinate and 2,4-difluorophenol is dissolved in a suitable solvent such as DMF. To the reaction mixture is added a suitable base such as potassium carbonate monohydrate and the heated at reflux for a period of 2 to 18 hours to yield [6-(2,4-Difluoro-phenoxy)-nicotinic acid methyl ester. The reaction is concentrated and purified according to techniques well known in the art. These resulting esters formed in Scheme E, Step 1 can be further elaborated to final compounds using the procedures described in Scheme B, step 2 and 3.

Intermediate 1

4-(5-Chloro-pentyloxy)-benzoic acid methyl ester

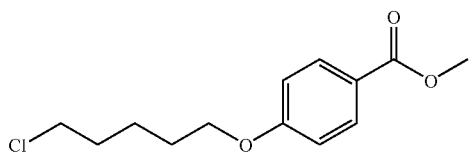

4-Hydroxy-benzoic acid methyl ester (1.52 g, 10 mmol), 5-chloro-1-pentanol (1.22 g, 10 mmol) and triphenylphosphine (2.62 g, 10 mmol) are dissolved in dry THF (30 mL) and cooled to 0° C. Diethylazodicarboxylate (DEAD) (1.74 g, 10 mmol) is dropped into this mixture at 0° C. and stirred at room temperature for 3 days. The reaction mixture is washed with brine, dried over $Na_2SO_4$, filtered and evaporated. The crude product is purified using silica-gel column chromatography ($CH_2Cl_2$ only to $CH_2Cl_2$:2 M $NH_3$ in MeOH=20:1) to give the desired product (1.14 g, 45%). NMR ($CDCl_3$): δ 7.98 (d, 2H, J=8.8 Hz), 6.89 (d, 2H, J=8.8 Hz), 4.02 (t, 2H, J=6.5 Hz), 3.88 (s, 3H), 3.57 (t, 2H, J=6.7 Hz), 1.85 (m, 4H), 1.64 (m, 2H).

Intermediate 2

4-(5-Chloro-pentyloxy)-benzoic acid

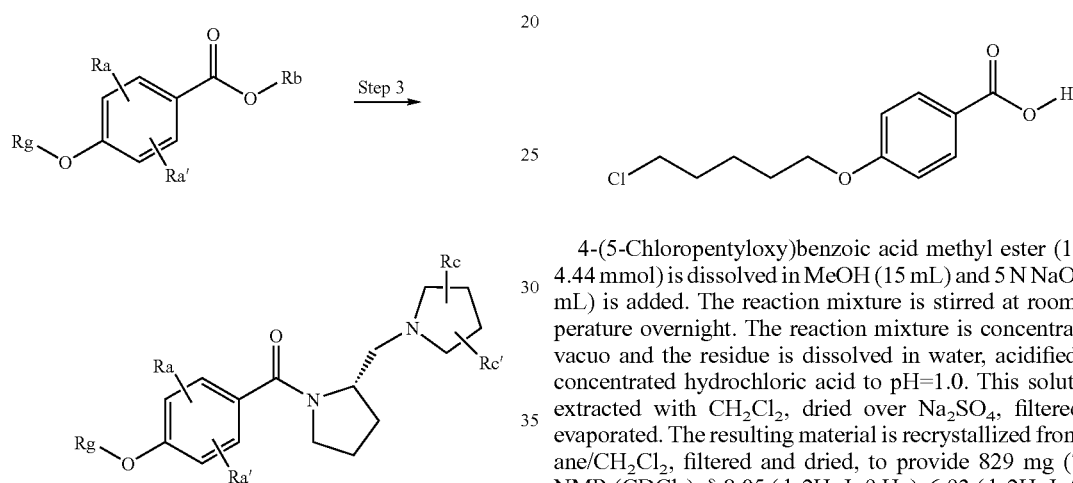

4-(5-Chloropentyloxy)benzoic acid methyl ester (1.14 g. 4.44 mmol) is dissolved in MeOH (15 mL) and 5 N NaOH (10 mL) is added. The reaction mixture is stirred at room temperature overnight. The reaction mixture is concentrated in vacuo and the residue is dissolved in water, acidified with concentrated hydrochloric acid to pH=1.0. This solution is extracted with $CH_2Cl_2$, dried over $Na_2SO_4$, filtered and evaporated. The resulting material is recrystallized from hexane/$CH_2Cl_2$, filtered and dried, to provide 829 mg (77%). NMR ($CDCl_3$): δ 8.05 (d, 2H, J=9 Hz), 6.93 (d, 2H, J=9 Hz), 4.05 (t, 2H, J=6 Hz), 3.57 (t, 2H, J=6 Hz), 4.85 (m, 4H), 1.65 (m, 2H).

Intermediate 3

4-(2-Hydroxy-ethoxy)-benzoic acid methyl ester

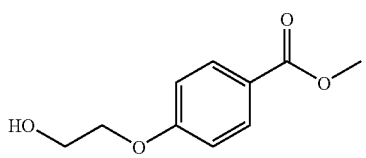

Methyl 4-hydroxybenzoate (1.52 g, 10 mmol), 2-chloroethanol (960 mg, 12 mmol), potassium iodide (100 mg, 0.6 mmol) and cesium carbonate (4.56 g, 14 mmol) are combined with dry THF (50 mL) and the reaction mixture is stirred under reflux for 24 h. Additional chloroethanol (960 mg), cesium carbonate (4.56 g) and potassium iodide (100 mg) are added to the mixture and stirred under reflux for 24 h. The reaction mixture is cooled to room temperature and water and $CH_2Cl_2$ are added. The separated $CH_2Cl_2$ layer is dried over $Na_2SO_4$, filtered and evaporated. The crude product is purified using silica-gel column chromatography (hexane: EtOAc=3:1) to give the titled compound (862 mg, 44%).

NMR (CDCl₃): δ 8.02 (d, 2H, J=9.0 Hz), 6.97 (d, 2H, J=9.0 Hz), 4.17 (t, 2H, J=5.0 Hz), 4.03 (m, 2H), 3.92 (s, 3H).

Intermediate 4

4-(2-Hydroxy-ethoxy)-benzoic acid

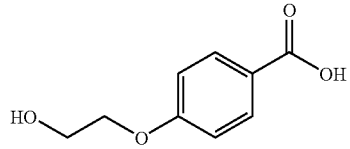

4-(2-Hydroxy-ethoxy)-benzoic acid methyl ester (400 mg, 2.04 mmol) is combined with a mixture of 1 N NaOH (3 mL) and MeOH (3 mL) and the mixture is stirred at 80° C. for 1 h. The solvents are evaporated and the resulting residue is dissolved in a small amount of water and acidified with 1 N HCl. The crystals are collected, washed with water, and dried to provide 154 mg (42%) of the titled compound. NMR (DMSO-d₆): δ 12.64 (br, 1H), 7.90 (d, 2H, J=8.2 Hz), 7.03 (d, 2H, J=8.2 Hz), 4.93 (br, 1H), 4.07 (t, 2H, J=4.9 Hz), 3.75 (m, 2H).

Intermediate 5

4-(3-Fluoro-propoxy)-benzoic acid methyl ester

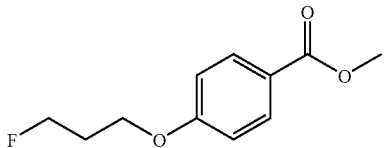

Procedure A: 4-Hydroxy-benzoic acid methyl ester (2.1 g, 13.8 mmol), 1-bromo-3-fluoro-propane (2.9 g, 20.7 mmol), and potassium carbonate (4.8 g, 34.5 mmol) are heated at reflux in acetone for 18 h. The reaction is cooled and filtered, and the solvent removed in vacuo. The crude mixture is dissolved in ethyl acetate and extracted with water (2×) and brine. The organic layer is dried over Na₂SO₄ and concentrated in vacuo. The product is purified by flash chromatography (10%-25% ethyl acetate/hexanes) to give 2.9 g (99%) of the title compound.

Intermediate 6

4-(3-Fluoro-propoxy)-benzoic acid lithium salt

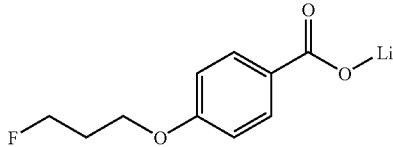

Procedure B: A mixture of 4-(3-fluoro-propoxy)-benzoic acid methyl ester (2.9 g, 13.7 mmol) and lithium hydroxide (0.36 g, 15 mmol) in a mixture of dioxane (40 mL) and water (20 mL) is stirred at room temperature for 24 h. The solvent is removed in vacuo to give the title compound as a white solid that was used without further purification. MS (ES−) 197.1.

Intermediate 7

4-(3-bromo-propoxy)-benzoic acid methyl ester

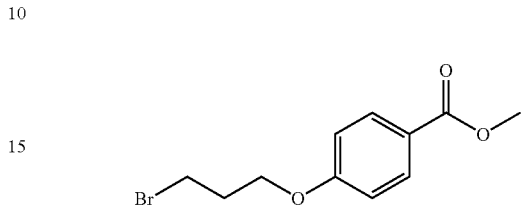

The title compound is prepared in a manner substantially analogous to Procedure A starting from 4-hydroxy-benzoic acid methyl ester and 1,3-dibromo-propane. MS (ES+) 272.9

Intermediate 8

4-(3-Methoxy-propoxy)-benzoic acid methyl ester

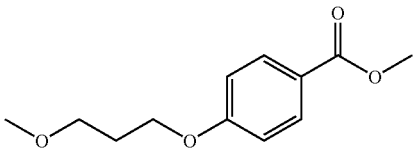

Procedure C: 4-(3-Bromo-propoxy)-benzoic acid methyl ester (0.63 g, 2.3 mmol) is dissolved in diethyl ether (15 mL), and solid NaOMe added (0.38 g, 7.0 mmol), and the mixture stirred at room temperature overnight. The solvent was removed in vacuo and the resulting residue is dissolved in ethyl acetate, washed with water (2×) and brine (2×). The organic layer is dried over Na₂SO₄ and evaporated. The crude material is purified by flash chromatography (0-20% ethyl acetate/hexane) to give 0.12 g (24%) of the title compound. MS (ES+) 225.0.

Intermediate 9

4-(3-Methanesulfonyl-propoxy)-benzoic acid methyl ester

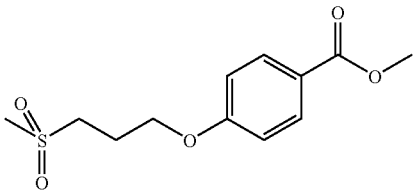

The title compound is prepared in a manner substantially analogous to Procedure C starting from 4-(3-bromo-propoxy)-benzoic acid methyl ester and methanesulfinic acid sodium salt using DMF as solvent. MS (ES+) 273.1.

Intermediate 10

(4-Bromo-phenyl)-(2-(S)-pyrrolidin-1-ylmethyl-pyrrolidin-yl)methanone

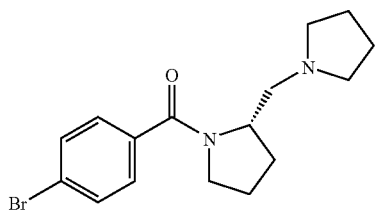

4-Bromobenzoic acid-2,5-dioxo-pyrrolidin-1-yl ester (3.5 g, 11.7 mmol, (CAS: 80586-82-9) and (S)-(+)-1-(2-pyrrolidinylmethyl)pyrrolidine are dissolved in tetrahydrofuran (0.15 M), and heated to reflux with stirring for 4 h. The reaction is allowed to cool to room temperature, diluted with water, and extracted with 10% isopropanol/dichloromethane. The organic portion is dried over sodium sulfate, filtered, and concentrated in vacuo. The crude material is purified on a silica column, eluting with 2 M ammonia in methanol and dichloromethane (93% yield with 80% purity). MS (m/e): 337.1 (M+1).

Intermediate 11

2-(R)-Methyl-1-(2-(S)-pyrrolidinylmethyl)pyrrolidine

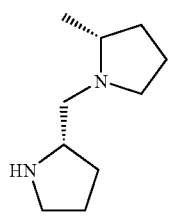

Equimolar amounts of (S) BOC proline (CAS 15761-39-4) and 2-(R)-methyl-pyrrolidine hydrochloride (CAS 135324-85-5) are coupled in a manner substantially analogous to Procedure D in dichloromethane to give 2(S)-(2(R)-methyl-pyrrolidine-1-carbonyl)-pyrrolidine-1-carboxylic acid tert-butyl ester. The material is deprotected by stirring in dichloromethane at 5-10° C. while trifluoroacetic acid (10 eq,) is added and then stirred at room temperature for 18 h. The reaction is concentrated, dissolved in $H_2O$, and the pH is adjusted to 8-9 with $K_2CO_3$. The extracts are extracted several times with $CH_2Cl_2$. The extracts are combined, dried ($Na_2SO_4$), filtered, and concentrated in vacuo to give (2(R)-methyl-pyrrolidin-1-yl)-pyrrolidin-2-yl-methanone. A 1 M lithium aluminum hydride/THF solution (3 eq.) is diluted with an equal volume of THF and stirred under $N_2$ as a THF solution of (2(R)-methyl-pyrrolidin-1-yl)-pyrrolidin-2-yl-methanone is added dropwise, allowing the reaction to mildly exotherm. The reaction mixture is stirred at 40° C. for 45 min, and then at room temperature 18 h. The mixture is cooled in an ice bath and quenched with $H_2O$ (3 eq.), 4 N NaOH (3 eq.), then $H_2O$ (9 eq.) while keeping the reaction temperature less than 15° C. The mixture is stirred overnight, filtered, and the precipitate is washed three times with THF. The filtrate and washes are combined and concentrated to give 2-(R)-methyl-1-(2-(S)-pyrrolidinylmethyl)pyrrolidine. MS (ES+) 169.3 $(M+H)^+$. The title compound is used as such or is purified by SCX chromatography or distillation.

Intermediate 12

1-Bromo-3-methanesulfonyl-benzene

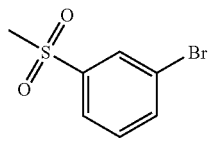

1-Bromo-3-methylsulfanyl-benzene (1.0 mmol) and 3-chloroperoxybenzoic acid (1.9 mmol), are combined in dichloromethane (0.1 M) in a 0° C. ice bath. The ice bath is removed and the reaction stirred at room temperature for one hour. Saturated aqueous sodium bicarbonate is added and the reaction extracted with dichloromethane. The organic portions are concentrated in vacuo and the resulting residue purified via radial silica chromatography, eluting with ethyl acetate and hexane.

Intermediate 13

4-(3-methanesulfonyl-phenoxy)-benzoic acid methyl ester

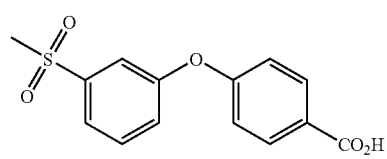

1-Bromo-3-methanesulfonyl-benzene (11.0 mmol) (see Intermediate 11) and 4-hydroxy-benzoic acid methyl ester (1.2 mmol) are dissolved in toluene (0.1M). Palladium acetate (0.02 mmol), biphenyl-2-yl-di-tert-butyl-phosphane (0.03 mmol) and tri-basic potassium phosphate (2.0 mmol) are added and the reaction heated reaction at 90° C. for 18 h. The reaction is allowed to cool to room temperature, washed with water while and then the aqueous extracted with dichloromethane. The organic portions are combined and concentrated in vacuo and purified by radial silica chromatography, eluting with ethyl acetate and hexane.

Intermediate 14

4-(3-Methanesulfonyl-phenoxy)-benzoic acid

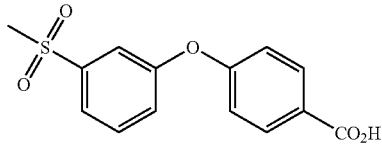

A stirred solution of 4-(3-methanesulfonyl-phenoxy)-benzoic acid methyl ester (1.0 mmol) (see Intermediate 12) in 1:1 methanol/tetrahydrofuran (0.15 M), is treated with 2 N sodium hydroxide (3.0 mmol) and heated to reflux for one hour. The reaction is concentrated in vacuo. 1 N Hydrochloric acid and water are added and the mixture extracted with 10% isopropanol/dichloromethane. The organic portion is concentrated in vacuo to yield the desired product. MS (m/e): 291.0 (M−1).

Intermediate 15

6-(2,4-Difluoro-phenoxy)-nicotinic acid methyl ester

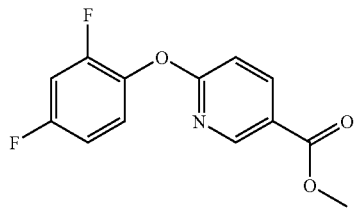

Procedure H: To a stirring solution of methyl-6-chloronicotinate (1.0 mmol) and potassium carbonate (3.0 mmol) in N,N-dimethylformamide (0.20 M), add 2,4-difluorophenol (1.5 mmol) and heat to 100° C. for 2 h. Allow to cool to room temperature, dilute the reaction with water, and extract with dichloromethane. Dry the organics with sodium sulfate, filter, and concentrate in vacuo. Purify via radial chromatography eluting with ethyl acetate and hexane. MS (m/e): 266.1 (M+1)

Intermediate 16

6-(2,4-Difluoro-phenoxy)-nicotinic acid sodium salt

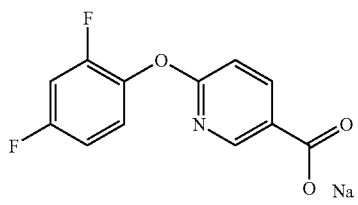

Procedure I: To a stirring solution of 6-(2,4-difluoro-phenoxy)-nicotinic acid methyl ester (See Intermediate 14) (1.0 mmol) in methanol/tetrahydrofuran (1:1) (0.15M), add 2N sodium hydroxide (1.02 mmol) and heat to reflux for four hours. After this time, remove the heat and concentrate in vacuo.

MS (m/e): 252.0 (M+1)

Example 1

(4-Hydroxy-phenyl)-(2-(S)-pyrrolidin-1-ylmethyl-pyrrolidin-1-yl)-methanone

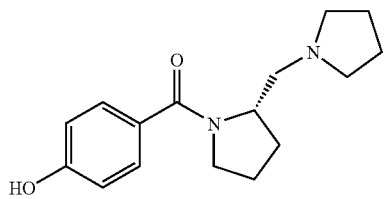

Procedure D: 4-Hydroxybenzoic acid (13.5 g, 97.9 mmol) is suspended in dichloromethane (400 mL). 1-Ethyl-3-[3-(dimethylamino)propyl]-carbodiimide hydrochloride (EDCI) (20.0 g, 104.3 mmol) and 1-hydroxybenzotriazole (HOBt) (14.1 g, 104.3 mmol) are added at room temperature in that order. N,N-diisopropylethylamine (28.4 mL, 163 mmol) and (S)(+)-1-(2-pyrrolidinylmethyl)pyrrolidine (10.0 g, 65.2 mmol) are added to the mixture. The mixture is stirred at room temperature overnight. Water is added and the mixture extracted with ethyl acetate. The product is water soluble, necessitating a number of organic extractions. The combined organic layers are dried over $Na_2SO_4$, filtered, and evaporated. The crude product is purified by silica-gel column chromatography (gradient: 100% $CH_2Cl_2$ to 10% 2M $NH_3$ in MeOH/$CH_2Cl_2$) to give the desired product (52%). MS (ES+): 275; $^1$H NMR (CDCl$_3$): δ 7.29 (bm, 2H), 6.76 (d, 2H), 4.50 (m, 1H), 3.52 (m, 2H), 2.90 (bm, 1H), 2.70 (bm, 4H), 2.04 (bm, 1H), 1.95 (bm, 2H), 1.67 (bm, 6H).

Example 2

S-(3-Fluoro-4-hydroxy-phenyl)-(2-(S)-pyrrolidin-1-ylmethyl-pyrrolidin-1-yl)-methanone

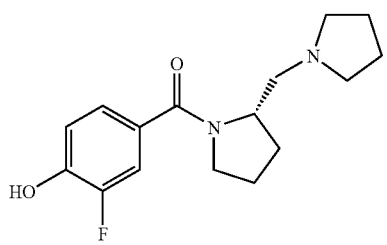

The title compound is prepared in a manner substantially analogous to Procedure D starting from 3-fluoro-4-hydroxybenzoic acid and (S)(+)-1-(2-pyrrolidinylmethyl)pyrrolidine. MS (ES+) 293.2

Example 3

S-(4-Butoxy-3-fluoro-phenyl)-(2-pyrrolidin-1-ylmethyl-pyrrolidin-1-yl)-methanone

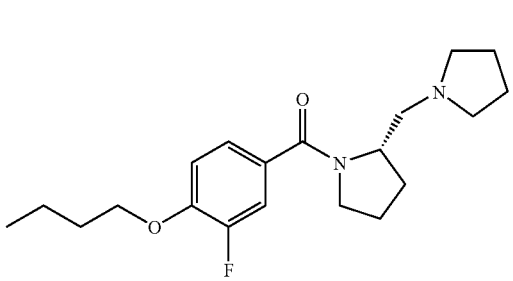

Procedure E: S-(3-Fluoro-4-hydroxy-phenyl)-(2-pyrrolidin-1-ylmethyl-pyrrolidin-1-yl)-methanone (0.193 g, 0.66 mmol) is dissolved in DMF (5 mL) and $Cs_2CO_3$ (0.43 g, 1.32 mmol) and 1-iodobutane (0.083 mL, 0.73 mmol) are added in succession. The reaction mixture is stirred at 90° C. for 12 h. Following aqueous workup, the crude material is purified by chromatography [SCX-MeOH wash, elute 2M $NH_3$/MeOH; then Varian 10 g $SiO_2$ cartridge, elute 10% (25/5/1 $CHCl_3$/MeOH/$NH_4OH$)/90% (10% MeOH/$CHCl_3$)] to give 60 mg (26%) of the title compound as a yellow oil. MS (ES+) 349.3.

Example 4

(4-Propoxy-phenyl)-(2-(S)-pyrrolidin-1-ylmethyl-pyrrolidin-1-yl)-methanone

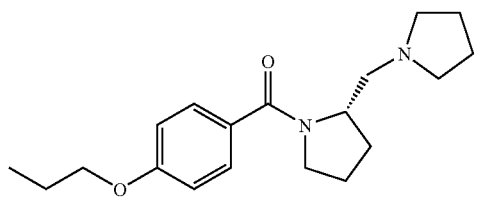

Procedure F: 4-Propoxybenzoic acid (180 mg, 1.00 mmol) is dissolved in 2.0 mL of thionyl chloride and stirred at 50° C. for 30 min. The excess thionyl chloride is removed in vacuo. The residue is dissolved in 1.0 mL of $CH_2Cl_2$. (S)(+)-1-(2-pyrrolidinylmethyl)pyrrolidine (164 mg, 1.07 mmol) and triethylamine (108 mg, 1.07 mmol) are dissolved in 3.0 mL of $CH_2Cl_2$ and cooled to 0° C. The acid chloride solution is added to this mixture and stirred at room temperature for 1 h. The reaction mixture is diluted with $CH_2Cl_2$, washed with brine, dried over $Na_2SO_4$, filtered and evaporated. The crude product is applied to silica-gel column chromatography ($CH_2Cl_2$: 2M $NH_3$ in MeOH=20:1) to provide 298 mg (94%) of the titled compound. Observed Mass: 317 (M+1).

Example 5

(4-Butoxy-phenyl)-(2-(S)-pyrrolidin-1-ylmethyl-pyrrolidin-1-yl)-methanone

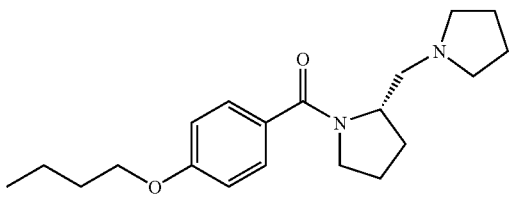

The title compound is prepared in a manner substantially analogous to Procedure F. Observed Mass 331.

Example 6

[4-(2-Chloro-ethoxy)-phenyl]-(2-(S)-pyrrolidin-1-ylmethyl-pyrrolidin-1-yl)-methanone

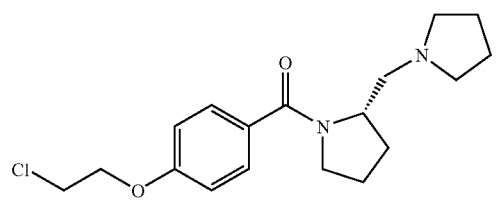

The title compound is prepared in a manner substantially analogous to Procedure F. Observed Mass 337.

Example 7

[4-(3-Chloro-propoxy)-phenyl]-(2-(S)-pyrrolidin-1-ylmethyl-pyrrolidin-1-yl)-methanone

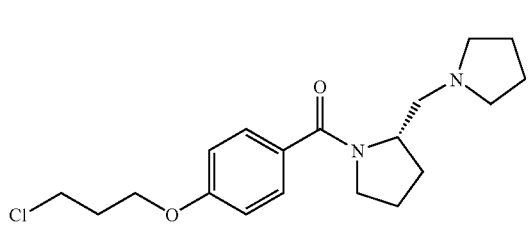

The title compound is prepared in a manner substantially analogous to Procedure F. Observed Mass 351.

Example 8

[4-(5-Chloro-pentyloxy)-phenyl]-(2-(S)-pyrrolidin-1-ylmethyl-pyrrolidin-1-yl)-methanone

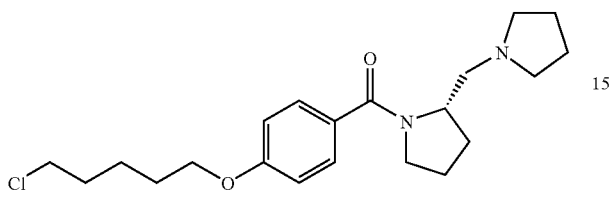

The title compound is prepared in a manner substantially analogous to Procedure F from 4-(5-chloro-pentyloxy)-benzoic acid. Observed Mass 379.

Example 9

(4-Butoxy-phenyl)-(2-(R)-pyrrolidin-1-ylmethyl-pyrrolidin-1-yl)-methanone

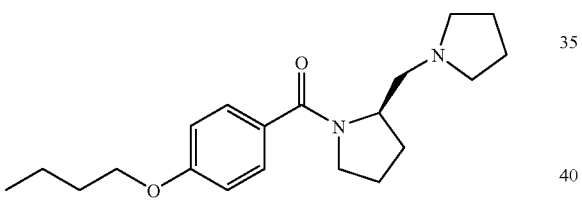

The title compound is prepared in a manner substantially analogous to Procedure F, using (R)-(−)-1-(2-pyrrolidinylmethyl)-pyrrolidine (CAS 60419-23-0). Observed Mass 331.

Example 10

[4-(3-Chloro-propoxy)-phenyl]-(2-(S)-pyrrolidin-1-ylmethyl-pyrrolidin-1-yl)-methanone

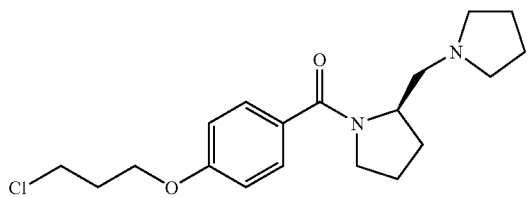

The title compound is prepared in a manner substantially analogous to Procedure F, using (R)-(−)-1-(2-pyrrolidinylmethyl)-pyrrolidine (CAS 60419-23-0). Observed Mass 351.

Example 11

(S)-(2-Pyrrolidin-1-ylmethyl-pyrrolidin-1-yl)-[4-(1,1,2,2-tetrafluoro-ethoxy)-phenyl]-methanone

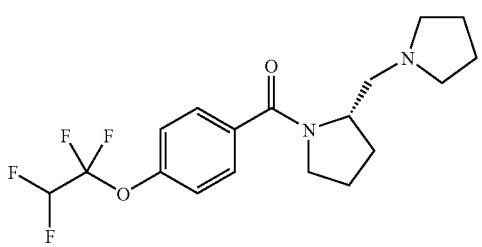

The title compound is prepared in a manner substantially analogous to Procedure F. Observed Mass 267.

Example 12

[4-(2-Hydroxy-ethoxy)-phenyl]-(2-(S)-pyrrolidin-1-ylmethyl-pyrrolidin-1-yl)-methanone

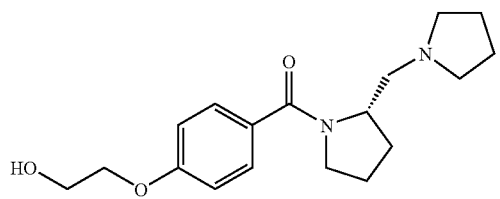

4-(2-Hydroxy-ethoxy)-benzoic acid (152 mg, 0.84 mmol), (S)(+)-1-(2-pyrrolidinylmethyl)pyrrolidine (193 mg, 1.25 mmol) and triethylamine (303 mg, 3.0 mmol) are dissolved in dichloromethane (5.0 mL) and benzotriazol-1-yloxytris(pyrrolidino)phosphonium hexafluorophosphate (PyBOP) (786 mg, 1.5 mmol) is added to the mixture. The mixture is stirred at room temperature for 3 days. The reaction mixture is diluted with dichloromethane, washed with brine, dried over Na$_2$SO$_4$, filtered and evaporated. The crude product is purified using silica-gel column chromatography (CH$_2$Cl$_2$:2M NH$_3$ in MeOH=20:1) to give 177 mg (66%) of the title compound. Observed Mass 319.

Example 13

[4-(3-Fluoro-propoxy)-phenyl]-(2-(S)-pyrrolidin-1-ylmethyl-pyrrolidin-1-yl)-methanone hydrochloride salt

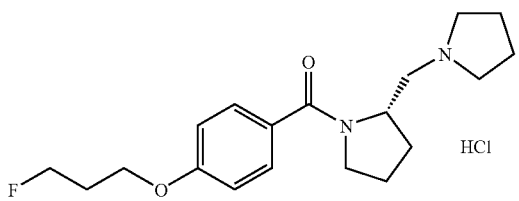

The title compound is prepared in a manner substantially analogous to Procedure D starting from 4-(3-fluoro-propoxy)-benzoic acid lithium salt and (S)(+)-1-(2-pyrrolidinylmethyl)pyrrolidine. The title compound is formed by treating [4-(3-fluoro-propoxy)-phenyl]-(2-pyrrolidin-1-ylmethyl-pyrrolidin-1-yl)-methanone with one equivalent of HCl in diethyl ether. MS (ES+) 335.2

Example 14

[4-(3-Methoxy-propoxy)-phenyl]-(2-(S)-pyrrolidin-1-ylmethyl-pyrrolidin-1-yl)-methanone trifluoroacetate salt

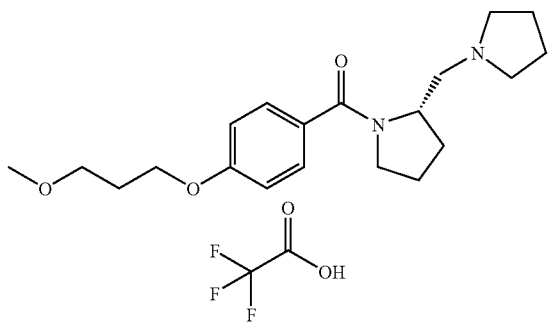

The title compound is prepared in a manner substantially analogous to Procedure B and D starting from 4-(3-methoxy-propoxy)-benzoic acid methyl ester and (S)(+)-1-(2-pyrrolidinylmethyl)pyrrolidine. The crude material was purified by reverse phase chromatography (19×250 mm Symmetry C18; 20-70% CH$_3$CN/H$_2$O with 0.1% TFA; 20 mL/min, 20 min run time) to provide the trifluoroacetate salt. MS (ES+) 347.2.

Example 15

[4-(3-Methanesulfonyl-propoxy)-phenyl]-(2-(S)-pyrrolidin-1-ylmethyl-pyrrolidin-1-yl)-methanone The title compound is prepared in a manner substantially analogous to Procedure B and D starting from 4-(3-methanesulfonyl-propoxy)-benzoic acid methyl ester and (S)(+)-1-(2-pyrrolidinylmethyl)pyrrolidine. MS (ES+) 395.3.

Example 16

[4-(3-Hydroxy-propoxy)-phenyl]-(2-(S)-pyrrolidin-1-ylmethyl-pyrrolidin-1-yl)-methanone The title compound is prepared in a manner substantially analogous to Procedures A, B and D starting from 4-hydroxy-benzoic acid methyl ester and 3-bromo-propan-1-ol. MS (ES+) 333.2.

Example 17

4-[4-(S)(+)-(2-Pyrrolidin-1-ylmethyl-pyrrolidine-1-carbonyl)-phenoxy]-butyric acid methyl ester

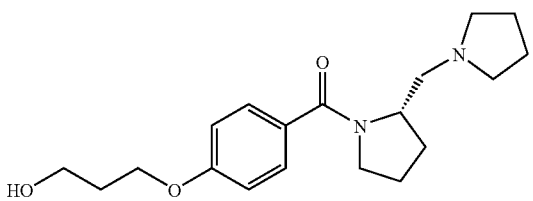

(4-Hydroxy-phenyl)-(2-pyrrolidin-1-ylmethyl-pyrrolidin-1-yl)-methanone (1.18 g, 4.3 mmol) and methyl bromobutyrate (0.7 mL, 5.4 mmol) are dissolved in DMF (20 mL) and stirred under nitrogen at room temperature as the cesium carbonate (2.80 g, 8.6 mmol) is added. The reaction mixture is stirred overnight. The reaction is diluted with CH$_2$Cl$_2$, filtered, washed with brine, dried over Na$_2$SO$_4$, filtered and evaporated. The crude product is partially purified by a SCX column (MeOH wash, elution with 2M NH$_3$ in MeOH. Further purification is accomplished using silica-gel column chromatography (gradient: 100% CH$_2$C 2 to 10% 2 M NH$_3$ in MeOH/CH$_2$Cl$_2$) to give 1.1 g (69%) of the title compound product. MS (ES+) 375.2 (M+H)$^+$.

Example 18

5-[4-(S)(+)-(2-Pyrrolidin-1-ylmethyl-pyrrolidine-1-carbonyl)-phenoxy]-pentanoic acid methyl ester

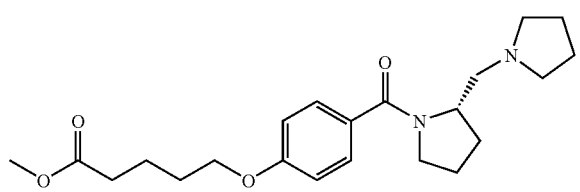

The title compound is prepared in a manner substantially analogous to Example 1 from (4-hydroxy-phenyl)-(2-pyrrolidin-1-ylmethyl-pyrrolidin-1-yl)-methanone (2.06 g, 7.5 mmol) and methyl bromovalerate (1.76 g, 9 mmol) to provide 2.2 g (75%). MS (ES+) 389.3 (M+H)$^+$.

Example 19

5-[4-(S)(+)-(2-Pyrrolidin-1-ylmethyl-pyrrolidine-1-carbonyl)-phenoxy]-pentanoic acid, lithium salt

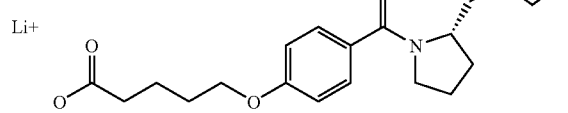

A dioxane (40 mL)/water (20 mL) solution of 5-[4-(2-pyrrolidin-1-ylmethyl-pyrrolidine-1-carbonyl)-phenoxy]-pentanoic acid methyl ester (2.91 g, 7.5 mmol) and lithium hydroxide monohydrate (349 mg, 8.3 mmol) is stirred at room temperature overnight. The reaction mixture is concentrated in vacuo to give the title compound (2.79 g, 98%). MS (ES+) 375.3 (M+H)$^+$.

Example 20

(6-Hydroxy-pyridin-3-yl)-(S)(+)-(2-pyrrolidin-1-ylmethyl-pyrrolidin-1-yl)-methanone

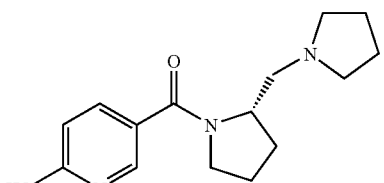

PS-carbodiimide (1.39 mmol/g) resin beads (2.1 g, 3 mmol) are added to a 10 mL CHCl$_3$/BuOH/MeCN (5:1:1) mixture of nicotinic acid (278 mg, 2 mmol), (S)(+)-1-(2-pyrrolidinylmethyl)pyrrolidine (231 mg, 1.5 mmol), HOBt (300 mg, 2.2 mmol), and triethylamine (0.30 mL, 2.2 mmol). The mixture is shaken at room temperature for 3 days. The reaction mixture is filtered and the beads are washed alternately with MeOH, then CH$_2$Cl$_2$, and the filtrate is concentrated in vacuo. The crude material product is partially purified by a SCX column (MeOH wash, elution with 2M NH$_3$ in MeOH. Further purification is accomplished using silica-gel column chromatography (gradient: 100% CH$_2$Cl$_2$ to 10% 2M NH$_3$ in MeOH/CH$_2$Cl$_2$) to give the title compound (200 mg, 73%). MS (ES+) 276.1 (M+H)$^+$.

Example 21

(6-Butoxy-pyridin-3-yl)-(S)(+)-(2-pyrrolidin-1-ylmethyl-pyrrolidin-1-yl)-methanone

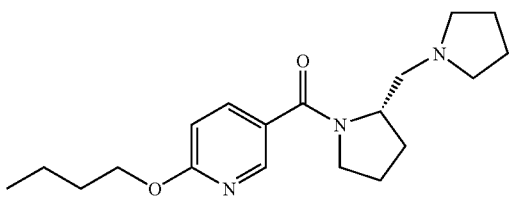

A mixture of (6-hydroxy-pyridin-3-yl)-(S)(+)-(2-pyrrolidin-1-ylmethyl-pyrrolidin-1-yl)-methanone (85 mg, 0.31 mmol), 1-bromo butane (0.04 mL, 0.36 mmol), cesium carbonate (195 mg, 0.60 mmol), and catalytic KI in dioxane (5 mL) is stirred under nitrogen at 80-90° C. for 10 h. The reaction is diluted with CH$_2$Cl$_2$, filtered, and washed with brine. The organic portion is dried over Na$_2$SO$_4$, filtered and evaporated. The crude product is partially purified by a SCX column (MeOH wash, elution with 2M NH$_3$ in MeOH. Further purification is accomplished using silica-gel column

Example 22

(2-(S)-Pyrrolidin-1-ylmethyl-pyrrolidin-1-yl)-[4-(4,4,4-trifluoro-butoxy)-phenyl]-methanone

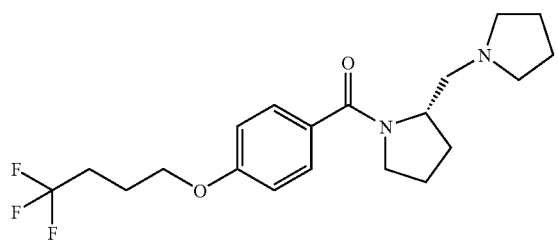

The title compound is prepared in a manner substantially analogous to Procedure E except the reaction mixture is stirred at room temperature overnight starting from (4-hydroxy-phenyl)-(2-(S)-pyrrolidin-1-ylmethyl-pyrrolidin-1-yl)-methanone and 1-bromo-4,4,4-trifluorobutane. MS (ES+) 385.2.

Example 23

[4-(5-Fluoro-pentyloxy)-phenyl]-(2-(S)-pyrrolidin-1-ylmethyl-pyrrolidin-1-yl)-methanone

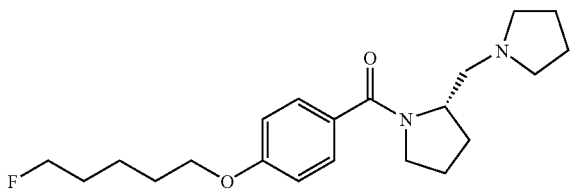

The title compound is prepared in a manner substantially analogous to Procedure E except the reaction mixture is stirred at room temperature overnight starting from (4-hydroxy-phenyl)-(2-(S)-pyrrolidin-1-ylmethyl-pyrrolidin-1-yl)-methanone and 1-bromo-5-fluoropentane. MS (ES+) 363.3

Example 24

[4-(4-Fluoro-butoxy)-phenyl]-(2-(S)-pyrrolidin-1-ylmethyl-pyrrolidin-1-yl)-methanone trifluoroacetate

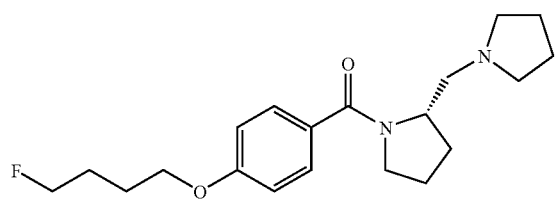

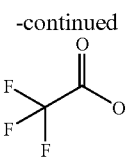

The title compound is prepared in a manner substantially analogous to Procedure E except the reaction mixture is stirred at room temperature overnight starting from (4-hydroxy-phenyl)-(2-(S)-pyrrolidin-1-ylmethyl-pyrrolidin-1-yl)-methanone and 1-bromo-4-fluorobutane. The crude material was purified by reverse phase chromatography (19×250 mm Symmetry C18; 20-70% CH₃CN/H₂O with 0.1% TFA; 20 mL/min, 20 min run time) to provide the trifluoroacetate salt. MS (ES+) 349.3

Example 25

[4-(2-Benzenesulfonyl-ethoxy)-phenyl]-(2-(S)-pyrrolidin-1-ylmethyl-pyrrolidin-1-yl)-methanone trifluoroacetate

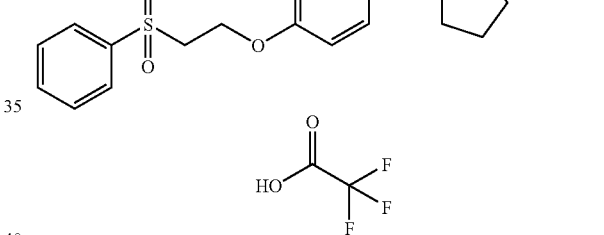

The title compound is prepared in a manner substantially analogous to Procedure E starting from (4-hydroxy-phenyl)-(2-(S)-pyrrolidin-1-ylmethyl-pyrrolidin-1-yl)-methanone and 2-chloroethylphenyl sulfone except potassium iodide (0.5 eq) is added and the reaction mixture is heated at 60° C. The crude material was purified by reverse phase chromatography (19×250 mm Symmetry C18; 20-70% CH₃CN/H₂O with 0.1% TFA; 20 mL/min, 20 min run time) to provide the trifluoroacetate salt. MS (ES+) 443.4.

Example 26

[4-(4-Methylsulfanyl-butoxy)-phenyl]-(2-(S)-pyrrolidin-1-ylmethyl-pyrrolidin-1-yl)-methanone trifluoroacetate

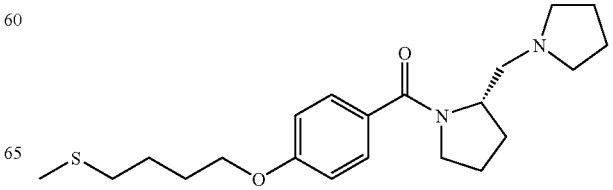

-continued

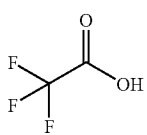

The title compound is prepared in a manner substantially analogous to Intermediate 1 starting from (4-hydroxy-phenyl)-(2-(S)-pyrrolidin-1-ylmethyl-pyrrolidin-1-yl)-methanone and 4-(methylthio)-1-butanol. The crude material was purified by reverse phase (19×250 mm Symmetry C18; 20-70% $CH_3CN/H_2O$ with 0.1% TFA; 20 mL/min, 20 min run time) to provide the trifluoroacetate salt. MS (ES+) 377.3.

Example 27

(2-(S)-Pyrrolidin-1-ylmethyl-pyrrolidin-1-yl)-[4-(3,3,3-trifluoro-propoxy)-phenyl]-methanone trifluoroacetate

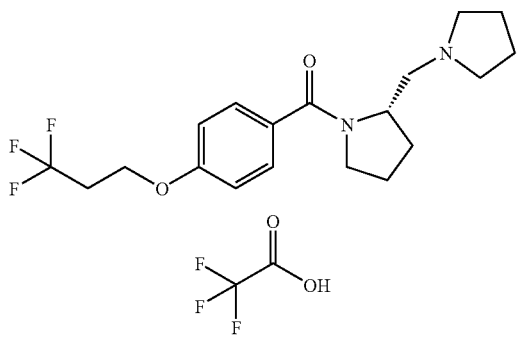

The title compound is prepared in a manner substantially analogous to Intermediate 1 starting from (4-hydroxy-phenyl)-(2-(S)-pyrrolidin-1-ylmethyl-pyrrolidin-1-yl)-methanone and 3,3,3-trifluoro-1-propanol. The crude material was purified by reverse phase (19×250 mm Symmetry C18; 20-70% $CH_3CN/H_2O$ with 0.1% TFA; 20 mL/min, 20 min run time) to provide the trifluoroacetate salt. MS (ES+) 371.3.

Example 28

(2-Fluoro-4-hydroxy-phenyl)-(2-(S)-pyrrolidin-1-ylmethyl-pyrrolidin-1-yl)-methanone

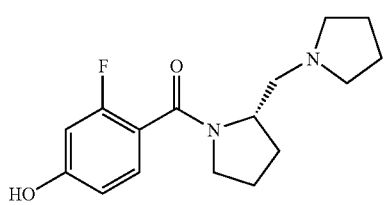

The title compound is prepared in a manner substantially analogous to Procedure D from 2-fluoro-4-hydroxybenzoic acid (CAS 65145-13-3). MS (ES+) 293.1.

Example 29

(2-Fluoro-4-hydroxy-phenyl)-[2-(S)-(2-(R)-methyl-pyrrolidin-1-ylmethyl)-pyrrolidin-1-yl]-methanone

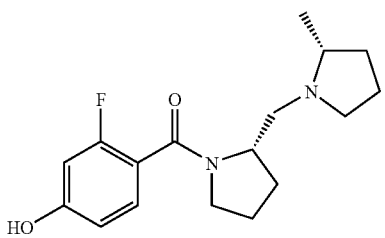

The title compound is prepared in a manner substantially analogous to Procedure D from 2-fluoro-4-hydroxy-benzoic acid and 2-(R)-methyl-1-(2-(S)-pyrrolidinylmethyl)pyrrolidine (Intermediate 11). MS (ES+) 307.3.

Example 30

(4-Pentyloxy-phenyl)-(2-(S)-pyrrolidin-1-ylmethyl-pyrrolidin-1-yl)-methanone

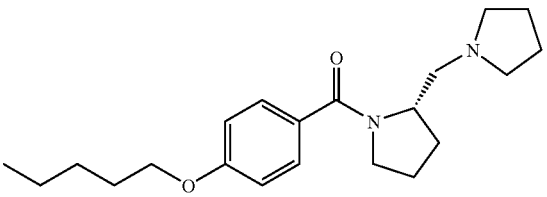

Procedure G: 4-Pentyloxybenzoic acid (67 mg, 0.32 mmol) and PS-carbodiimide (484 mg, 0.64 mmol, mmol/g=1.32) are combined with 5% DMF in $CH_2Cl_2$ (5.0 mL) and the mixture is stirred. (S)(+)-1-(2-pyrrolidinylmethyl)pyrrolidine (50 mg, 0.32 mmol) is added to this mixture and stirred at room temperature overnight. The reaction mixture is filtered and the resin is washed with $CH_2Cl_2$. The filtrate is concentrated and the resulting residue purified using silica-gel column chromatography (in $CH_2Cl_2$ followed by 5% 2 M $NH_3$ MeOH in $CH_2Cl_2$) to give 28.9 mg (26%) of the title compound.

Observed mass: 345 (M+1).

Example 31

5-Methoxy-2-methylene-1-(2-(S)-pyrrolidin-1-ylm-ethyl-pyrrolidin-1-yl)-pent-3-en-1-one

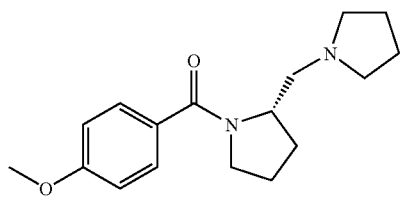

The title compound is prepared in a manner substantially analogous to Procedure G. Observed Mass 289.

Example 32

(4-Isobutoxy-phenyl)-(2-(S)-pyrrolidin-1-ylmethyl-pyrrolidin-1-yl)-methanone

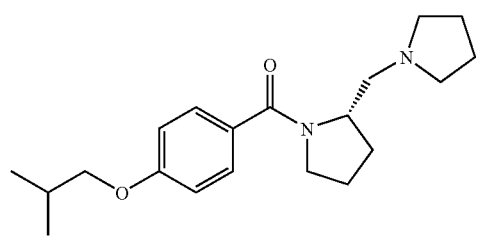

The title compound is prepared in a manner substantially analogous to Procedure G. Observed Mass 331.

Example 33

(4-Isopropoxy-phenyl)-(2-(S)-pyrrolidin-1-ylmethyl-pyrrolidin-1-yl)-methanone

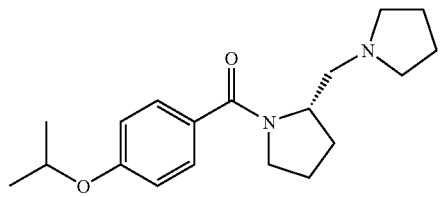

The title compound is prepared in a manner substantially analogous to Procedure G. Observed Mass 317.

Example 34

(4-Cyclohexylmethoxy-phenyl)-(2-(S)-pyrrolidin-1-ylmethyl-pyrrolidin-1-yl)-methanone

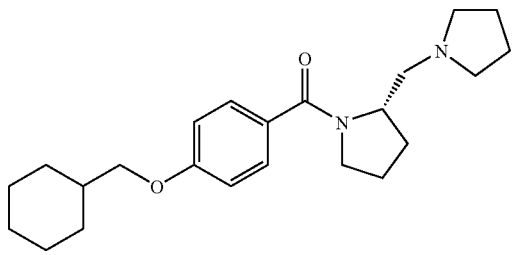

The title compound is prepared in a manner substantially analogous to Procedure G. Observed Mass 371.

Example 35

(4-Heptyloxy-phenyl)-(2-(S)-pyrrolidin-1-ylmethyl-pyrrolidin-1-yl)-methanone

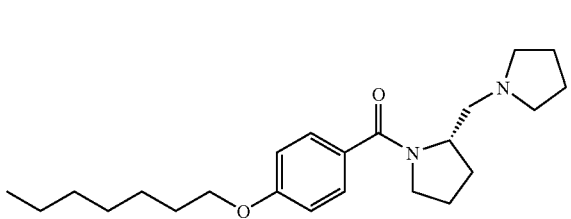

The title compound is prepared in a manner substantially analogous to Procedure G. Observed Mass 373.

Example 36

(4-Difluoromethoxy-phenyl)-(2-(S)-pyrrolidin-1-ylmethyl-pyrrolidin-1-yl)-methanone

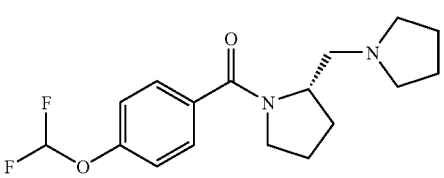

The title compound is prepared in a manner substantially analogous to Procedure G. Observed Mass 325.

Example 37

(4-Ethoxy-phenyl)-(2-(S)-pyrrolidin-1-ylmethyl-pyrrolidin-1-yl)-methanone

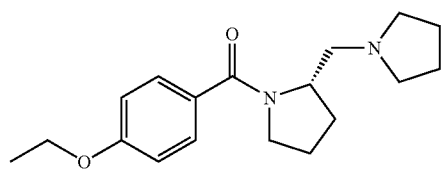

The title compound is prepared in a manner substantially analogous to Procedure G. Observed Mass 303.

Example 38

(4-Hexyloxy-phenyl)-(2-(S)-pyrrolidin-1-ylmethyl-pyrrolidin-1-yl)-methanone

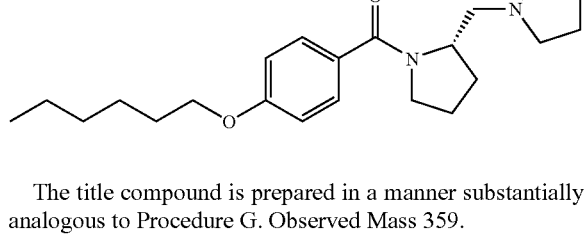

The title compound is prepared in a manner substantially analogous to Procedure G. Observed Mass 359.

Example 39

(S)-(2-Pyrrolidin-1-ylmethyl-pyrrolidin-1-yl)-(4-trifluoromethoxy-phenyl)-methanone

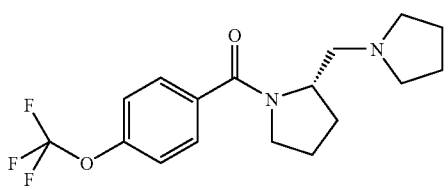

The title compound is prepared in a manner substantially analogous to Procedure G. Observed Mass 343.

Example 40

[4-(2-Butoxy-ethoxy)-phenyl]-(2-(S)-pyrrolidin-1-ylmethyl-pyrrolidin-1-yl)-methanone

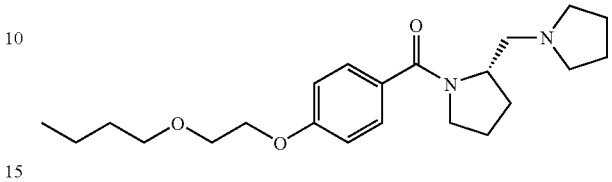

The title compound is prepared in a manner substantially analogous to Procedure G. Observed Mass 375.

Example 41

[4-(2-Phenoxy-ethoxy)-phenyl]-(2-(S)-pyrrolidin-1-ylmethyl-pyrrolidin-1-yl)-methanone

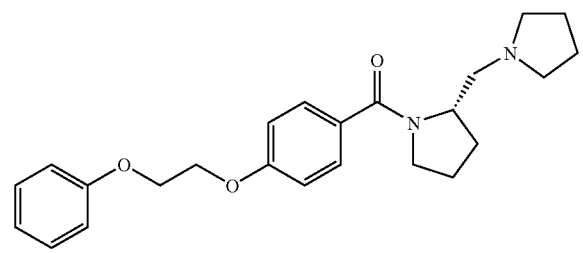

The title compound is prepared in a manner substantially analogous to Procedure G. Observed Mass 395.

Example 42

(4-Cyclopentyloxy-phenyl)-(2-(S)-pyrrolidin-1-ylmethyl-pyrrolidin-1-yl)-methanone

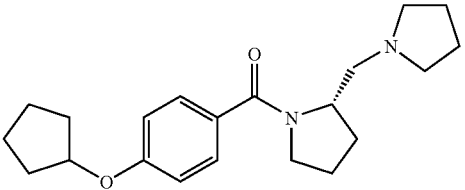

The title compound is prepared in a manner substantially analogous to Procedure G. Observed Mass 343.

Example 43

[4-(3-Methyl-butoxy)-phenyl]-(2-(S)-pyrrolidin-1-ylmethyl-pyrrolidin-1-yl)-methanone

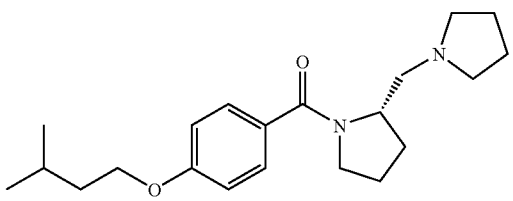

The title compound is prepared in a manner substantially analogous to Procedure G. Observed Mass 345.

Example 44

(4-But-3-enyloxy-phenyl)-(2-(S)-pyrrolidin-1-ylmethyl-pyrrolidin-1-yl)-methanone

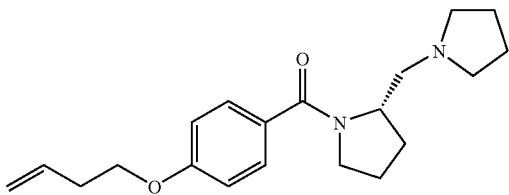

The title compound is prepared in a manner substantially analogous to Procedure G. Observed Mass 329.

Example 45

[4-(Cyclohex-2-enyloxy)-phenyl]-(2-(S)-pyrrolidin-1-ylmethyl-pyrrolidin-1-yl)-methanone

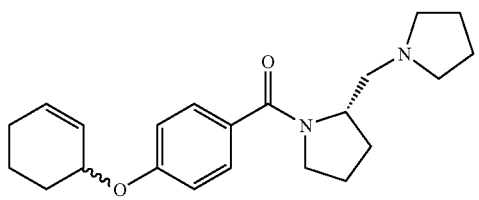

The title compound is prepared in a manner substantially analogous to Procedure G. Observed Mass 355.

Example 46

[4-(3-Phenyl-propoxy)-phenyl]-(2-(S)-pyrrolidin-1-ylmethyl-pyrrolidin-1-yl)-methanone

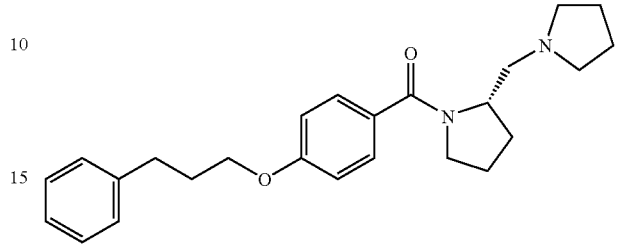

The title compound is prepared in a manner substantially analogous to Procedure G. Observed Mass 393.

Example 47

[4-(3-Phenyl-propoxy)-phenyl]-(2-(S)-pyrrolidin-1-ylmethyl-pyrrolidin-1-yl)-methanone, hydrochloride salt

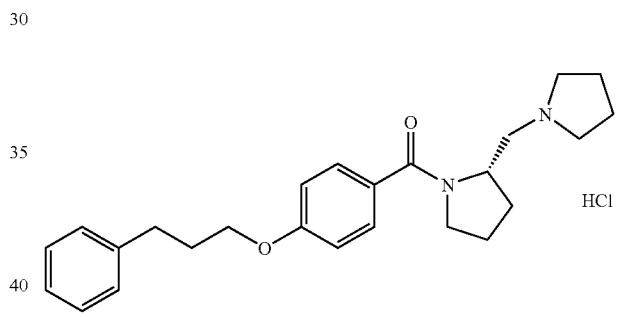

The title compound is formed by treating [4-(3-Phenyl-propoxy)-phenyl]-(2-pyrrolidin-1-ylmethyl-pyrrolidin-1-yl)-methanone with one equivalent of HCl in diethyl ether. Observed Mass 393.

Example 48

(4-Phenoxy-phenyl)-(2-(S)-pyrrolidin-1-ylmethyl-pyrrolidin-1-yl)-methanone

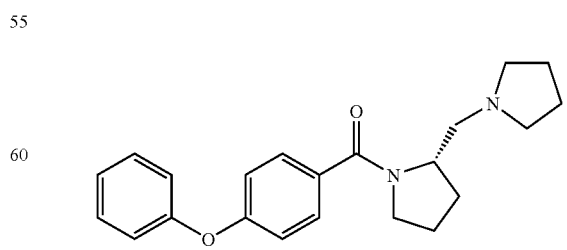

The title compound is prepared in a manner substantially analogous to Procedure G. Observed Mass 351.

Example 49

[4-(4-Phenoxy-butoxy)-phenyl]-(2-(S)-pyrrolidin-1-ylmethyl-pyrrolidin-1-yl)-methanone trifluoroacetate

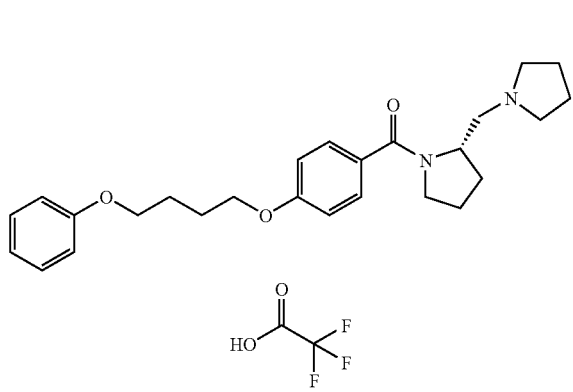

The title compound is prepared in a manner substantially analogous to Procedure E the reaction mixture is stirred at room temperature overnight starting from (4-hydroxy-phenyl)-(2-(S)-pyrrolidin-1-ylmethyl-pyrrolidin-1-yl)-methanone and 4-pheanoxybutyl bromide. The crude material is purified by reverse phase chromatography (19×250 mm Symmetry C18; 20-70% CH$_3$CN/H$_2$O with 0.1% TFA; 20 mL/min, 20 min run time) to provide the trifluoroacetate salt. MS (ES+) 423.4

Example 50

[4-(3-Phenoxy-propoxy)-phenyl]-(2-(S)-pyrrolidin-1-ylmethyl-pyrrolidin-1-yl)-methanone trifluoroacetate

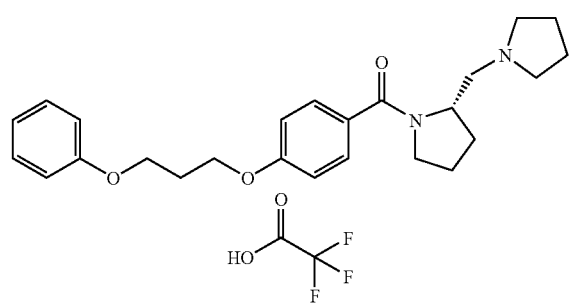

The title compound is prepared in a manner substantially analogous to Procedure E except the reaction mixture is stirred at room temperature overnight starting from (4-hydroxy-phenyl)-(2-(S)-pyrrolidin-1-ylmethyl-pyrrolidin-1-yl)-methanone and 3-phenoxypropyl bromide. The crude material is purified by reverse phase chromatography (19× 250 mm Symmetry C18; 20-70% CH$_3$CN/H$_2$O with 0.1% TFA; 20 mL/min, 20 min run time) to provide the trifluoroacetate salt. MS (ES+) 409.4

Example 51

{4-[3-(4-Methoxy-phenyl)-propoxy]-phenyl}-(2-(S)-pyrrolidin-1-ylmethyl-pyrrolidin-1-yl)-methanone trifluoroacetate

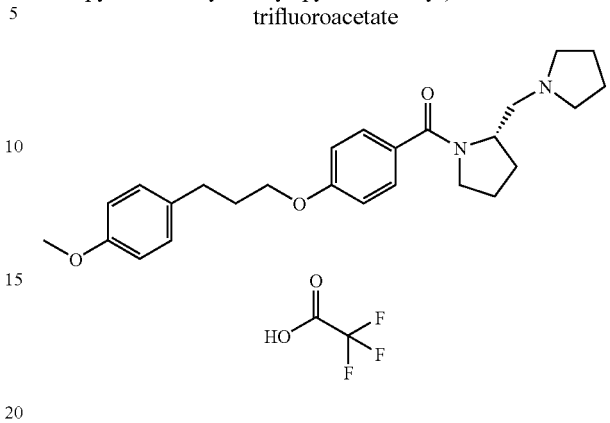

The title compound is prepared in a manner substantially analogous to Procedure E, starting from (4-hydroxy-phenyl)-(2-(S)-pyrrolidin-1-ylmethyl-pyrrolidin-1-yl)-methanone and 1-(3-chloro-propyl)-4-methoxy-benzene except potassium iodide (0.5 eq) is added and the reaction mixture is stirred at room temperature. The crude material is purified by reverse phase chromatography (19×250 mm Symmetry C18; 20-70% CH$_3$CN/H$_2$O with 0.1% TFA; 20 mL/min, 20 min run time) to provide the trifluoroacetate salt. MS (ES+) 423.4.

Example 52

[4-(3-Methanesulfonyl-phenoxy)-phenyl]-(2-(S)-pyrrolidin-1-ylmethyl-pyrrolidin-1-yl)-methanone hydrochloride

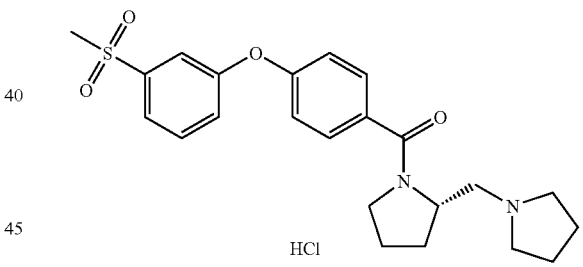

4-(3-Methanesulfonyl-phenoxy)-benzoic acid (1.0 mmol) (see Intermediate 13) and oxalyl chloride (2.0 mmol) are combined in dichloromethane (0.10 M), add 1 drop of dimethylformamide added as a catalyst. The solution is stirred at room temperature for 2 h. The reaction is concentrated in vacuo. The resulting residue is dissolved in dichloromethane and added to a stirring solution of (S)-(+)-1-(2-pyrrolidinyl-methyl)pyrrolidine (1.0 mmol) and N-methylmorpholine (1.0 mmol) in dichloromethane (0.10 M). The reaction is stirred at room temperature for 18 h. The reaction is washed with saturated aqueous sodium bicarbonate and the aqueous portion extracted with 10% isopropanol/dichloromethane. The combined organic portions are concentrated in vacuo and purified via radial chromatography eluting with 2 M ammonia in methanol and dichloromethane. The purified free base is dissolved in a minimal amount of dichloromethane and a slight excess of 1 M HCl in ether is added, followed by hexane. The mixture is then concentrated in vacuo to give the titled compound. MS (m/e): 429.2 (M+1)

Example 53

[4-(4-Methanesulfonyl-phenoxy)-phenyl]-(2-(S)-pyrrolidin-1-ylmethyl-pyrrolidin-1-yl)-methanone hydrochloride

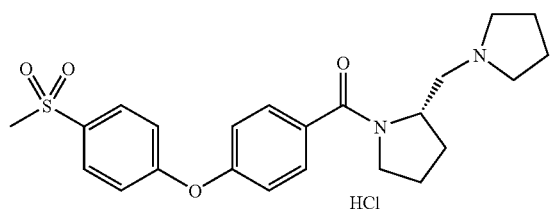

Combine (4-bromo-phenyl)-(2-(S)-pyrrolidin-1-ylmethyl-pyrrolidin-yl)methanone (see Intermediate 10) (1.35 mmol), 4-methylsulfonylphenol (1.0 mmol), potassium carbonate (1.65 mmol), and copper (0.022 mmol) in dimethylformamide (0.4 M) and heat at reflux temperature for 48 h. The reaction is allowed to cool to room temperature, diluted with water, and extracted with 10% isopropanol/dichloromethane. The organic portion is concentrated in vacuo. The resulting residue is purified by radial silica chromatography, eluting with 2 M ammonia in methanol and dichloromethane. The purified free base is dissolved in a minimal amount of dichloromethane and a slight excess of 1 M HCl in ether is added, followed by hexane. The material is concentrated in vacuo to give the titled compound. MS (m/e): 429.2 (M+1).

Example 54

(S)-[6-(2,4-Difluoro-phenoxy)-pyridin-3-yl]-(2-pyrrolidin-1-ylmethyl-pyrrolidin-1-yl)-methanone dihydrochloride salt

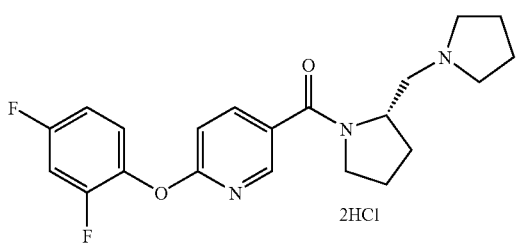

Procedure J: To a stirring solution of 6-(2,4-difluoro-phenoxy)-nicotinic acid sodium salt (1.0 mmol) and N-methyl morpholine (1.0 mmol) in dichloromethane (0.10 M) in a 0° C. ice bath, add 2-chloro-4,6-dimethoxy-1,3,5-triazine (1.0 mmol). Remove the ice bath and stir for 45 min. Add (S)-(+)-1-(2-pyrrolidinylmethyl)pyrrolidine (11.0 mmol) and stir at room temperature for 18 h. Wash the reaction with saturated aqueous sodium bicarbonate while extracting with 10% isopropanol/dichloromethane. Dry the organic layer with sodium sulfate, filter and concentrate in vacuo. Purify via chromatography eluting with 2M ammonia in methanol and dichloromethane. Dissolve the purified free base in minimal dichloromethane and add 1 M HCl in ether in slight excess followed by hexane. Concentrate in vacuo to give the titled compound. MS (m/e): 388.2 (M+1)

Example 55

(S)-(2-Pyrrolidin-1-ylmethyl-pyrrolidin-1-yl)-[6-(4-trifluoromethoxy-phenoxy)-pyridin-3-yl]-methanone dihydrochloride salt

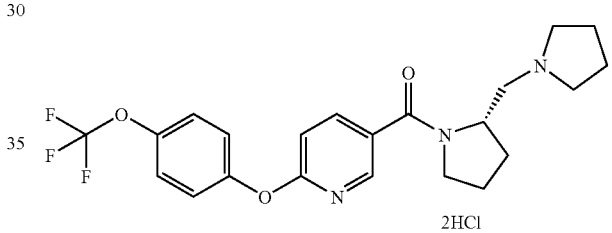

The title compound is prepared in a manner substantially analogous to procedures H, I, and J starting from methyl-6-chloronicotinate and 4-trifluoromethoxy-phenol. MS (m/e): 436.2 (M+1).

Further embodiments of the invention include the compounds of formulae X1 to X52 in Table 1 below. A further embodiment of the invention are any novel intermediate preparations described herein which are useful for preparing the histamine H3 receptor antagonists or inverse agonists of formula I, or II, or X1 to X52.

TABLE 1

| Formula Number | Structure |
|---|---|
| X1 | ![structure] |

TABLE 1-continued
| Formula Number | Structure |
|---|---|
| X2 | 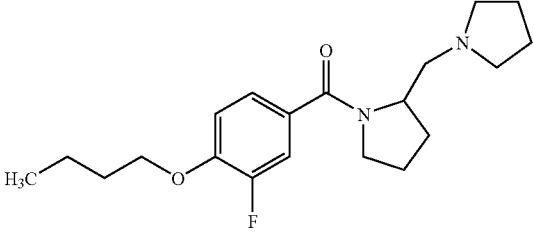 |
| X3 | 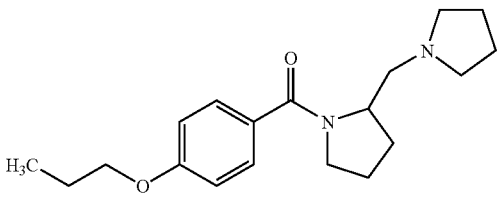 |
| X4 | 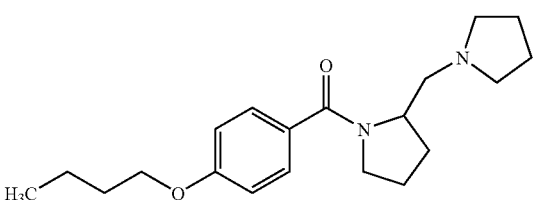 |
| X5 | 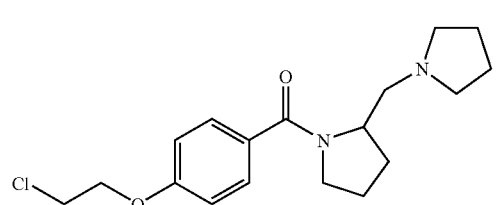 |
| X6 | 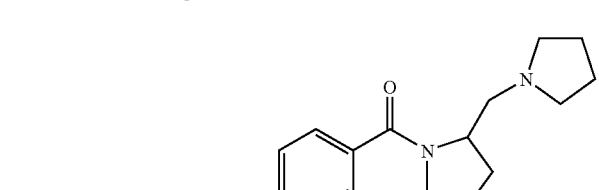 |
| X7 | 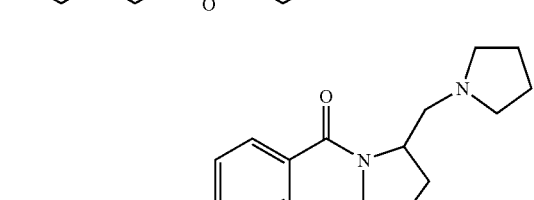 |
| X8 | 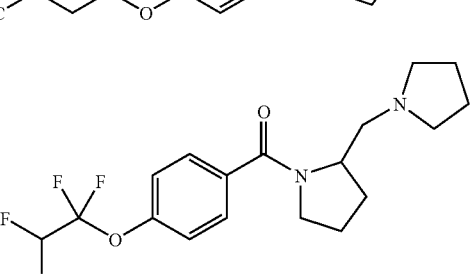 |

TABLE 1-continued
| Formula Number | Structure |
|---|---|
| X9 | 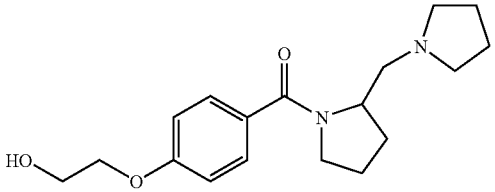 |
| X10 | 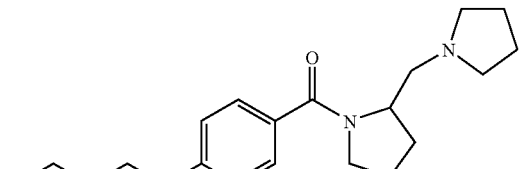 |
| X11 | 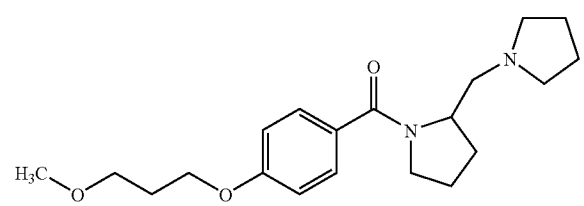 |
| X12 | 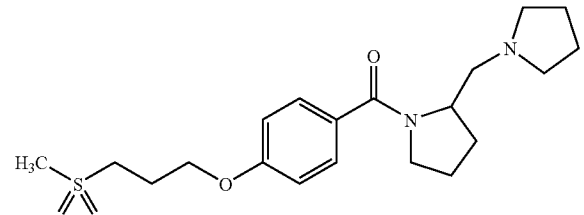 |
| X13 | 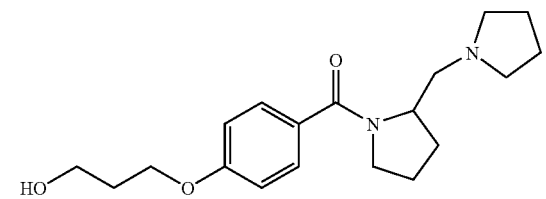 |
| X14 | 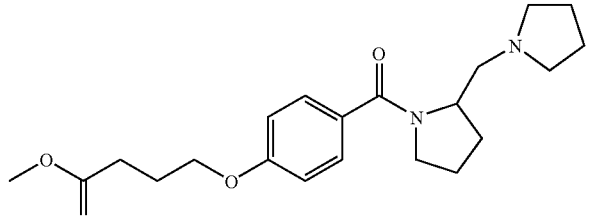 |
| X15 | 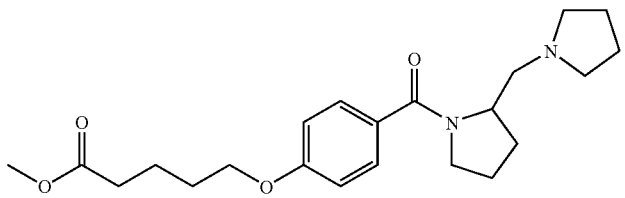 |

TABLE 1-continued

| Formula Number | Structure |
|---|---|
| X16 | (structure: Li⁺ ⁻O-C(=O)-CH₂CH₂CH₂-O-C₆H₄-C(=O)-N(pyrrolidine with CH₂-pyrrolidinyl)) |
| X17 | (structure: 6-hydroxypyridine-3-carbonyl-[2-(pyrrolidin-1-ylmethyl)pyrrolidine]) |
| X18 | (structure: 6-butoxypyridine-3-carbonyl-[2-(pyrrolidin-1-ylmethyl)pyrrolidine]) |
| X19 | (structure: 6-(4,4,4-trifluorobutoxy)pyridine-3-carbonyl-[2-(pyrrolidin-1-ylmethyl)pyrrolidine]) |
| X20 | (structure: 4-(5-fluoropentyloxy)benzoyl-[2-(pyrrolidin-1-ylmethyl)pyrrolidine]) |
| X21 | (structure: 4-(4-fluorobutoxy)benzoyl-[2-(pyrrolidin-1-ylmethyl)pyrrolidine]) |
| X22 | (structure: 4-[2-(phenylsulfonyl)ethoxy]benzoyl-[2-(pyrrolidin-1-ylmethyl)pyrrolidine]) |

TABLE 1-continued

| Formula Number | Structure |
|---|---|
| X23 | 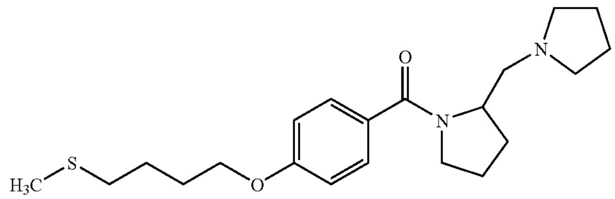 |
| X24 | 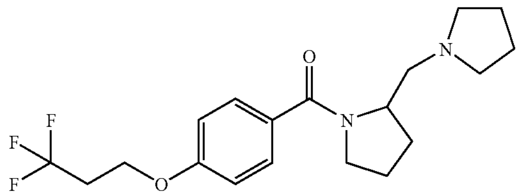 |
| X25 | 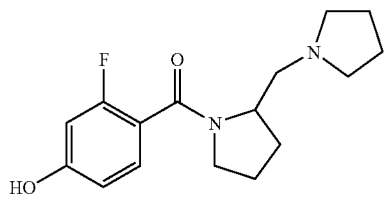 |
| X26 | 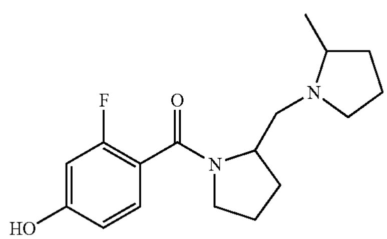 |
| X27 | 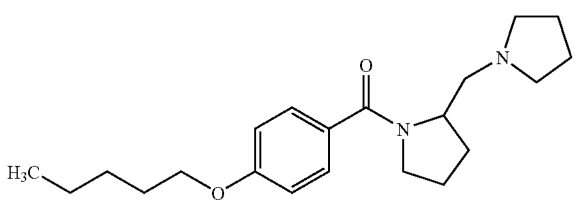 |
| X28 | 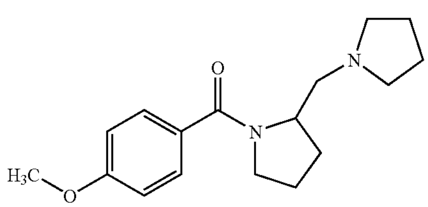 |
| X29 | 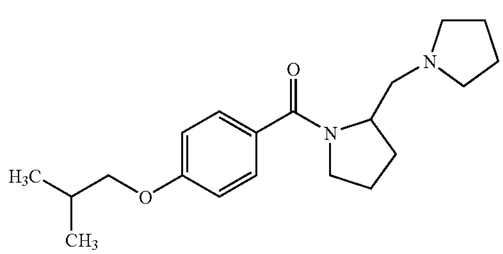 |

TABLE 1-continued

| Formula Number | Structure |
|---|---|
| X30 | 4-isopropoxyphenyl-[2-(pyrrolidin-1-ylmethyl)pyrrolidin-1-yl]methanone |
| X31 | [4-(cyclohexylmethoxy)phenyl]-[2-(pyrrolidin-1-ylmethyl)pyrrolidin-1-yl]methanone |
| X32 | [4-(heptyloxy)phenyl]-[2-(pyrrolidin-1-ylmethyl)pyrrolidin-1-yl]methanone |
| X33 | [4-(difluoromethoxy)phenyl]-[2-(pyrrolidin-1-ylmethyl)pyrrolidin-1-yl]methanone |
| X34 | (4-ethoxyphenyl)-[2-(pyrrolidin-1-ylmethyl)pyrrolidin-1-yl]methanone |
| X35 | [4-(hexyloxy)phenyl]-[2-(pyrrolidin-1-ylmethyl)pyrrolidin-1-yl]methanone |
| X36 | [4-(trifluoromethoxy)phenyl]-[2-(pyrrolidin-1-ylmethyl)pyrrolidin-1-yl]methanone |

TABLE 1-continued

| Formula Number | Structure |
|---|---|
| X37 | 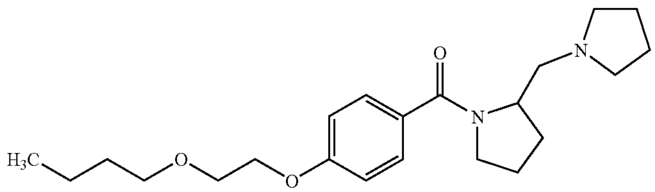 |
| X38 | 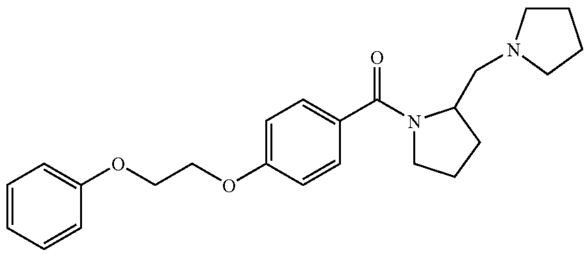 |
| X39 | 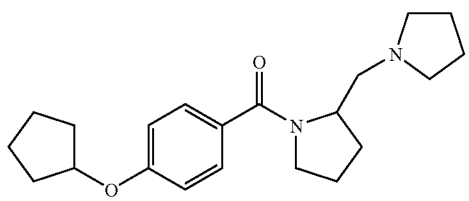 |
| X40 | 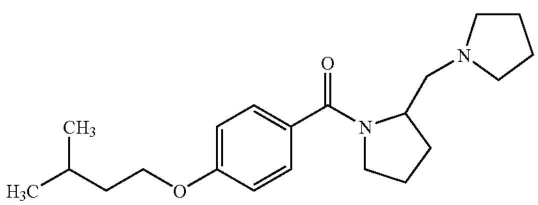 |
| X41 | 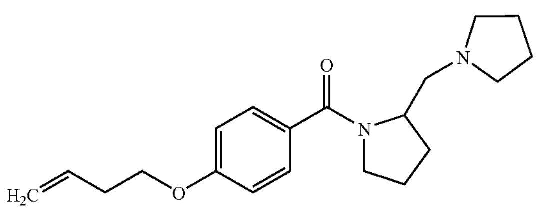 |
| X42 | 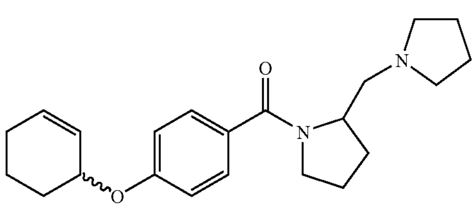 |
| X43 | 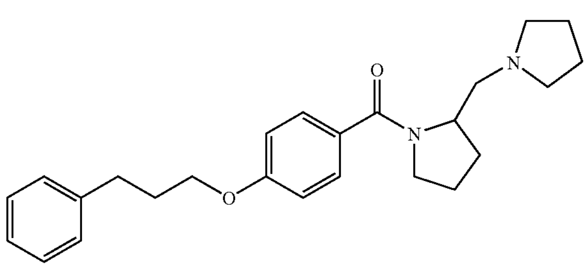 |

TABLE 1-continued
| Formula Number | Structure |
|---|---|
| X44 | 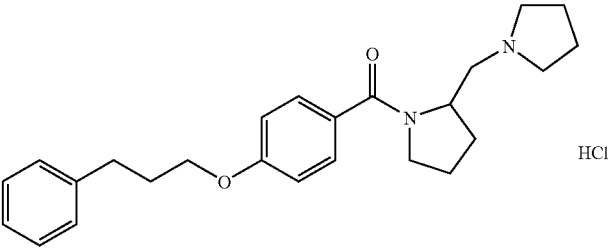 HCl |
| X45 | 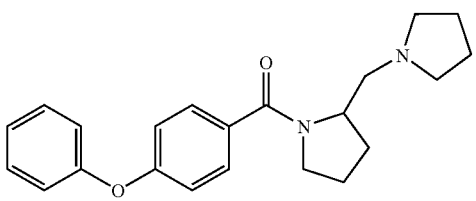 |
| X46 | 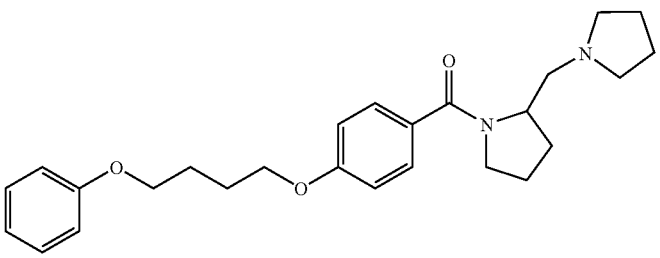 |
| X47 | 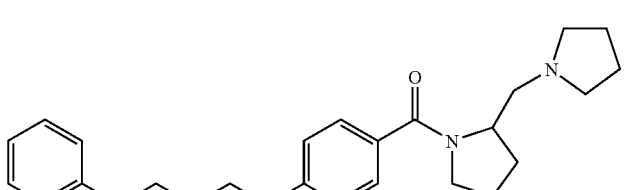 |
| X48 | 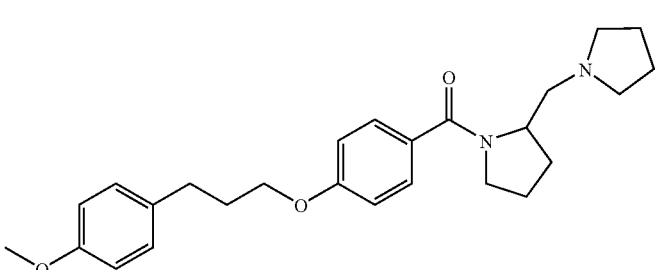 |
| X49 | 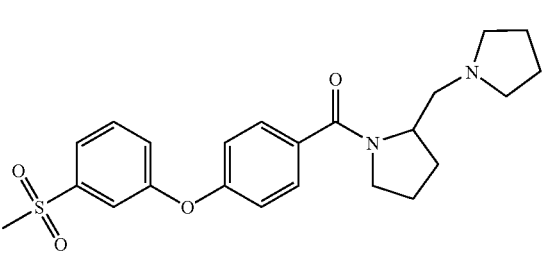 |

TABLE 1-continued

| Formula Number | Structure |
|---|---|
| X50 | 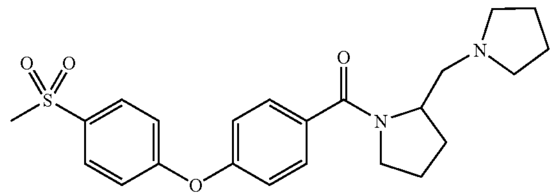 |
| X51 | 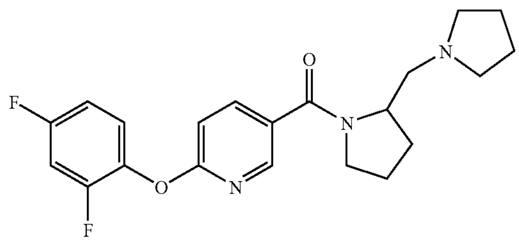 |
| X52 | 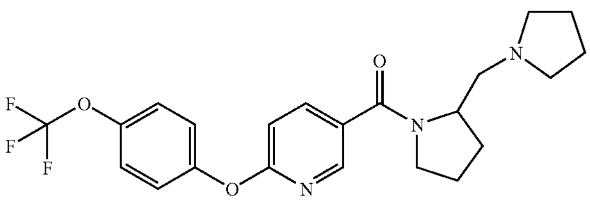 |

The pharmaceutical salts of the invention are typically formed by reacting a compound of Formula I or Formula II with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

The optimal time for performing the reactions of the Schemes, Preparations, and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I or Formula II may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The compound of Formula I or Formula II is preferably formulated in a unit dosage form prior to administration. Therefore, yet another embodiment of the present invention is a pharmaceutical composition comprising a compound of Formula I or Formula II and one or more pharmaceutically acceptable carriers, diluents or excipients.

The present pharmaceutical compositions are prepared by known procedures using well-known and readily available ingredients. In making the formulations of the present invention, the active ingredient (Formula I or Formula II compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as a re conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Compounds of Formula I or Formula II are effective as antagonists or inverse agonists of the histamine H3 receptor, and thus inhibit the activity of the H3 receptor. More particularly, these compounds are selective antagonists or inverse agonists of the histamine H3 receptor. As selective antagonists or inverse agonists, the compounds of Formula I or Formula II are useful in the treatment of diseases, disorders, or conditions responsive to the inactivation of the histamine H3 receptor, including but not limited to obesity and other eating-related disorders, and cognitive disorders. It is postulated that selective antagonists or inverse agonists of H3R will raise brain histamine levels and possibly that of other monoamines resulting in inhibition of food consumption while minimizing peripheral consequences. Although a number of H3R antagonists are known in the art, none have proven to be satisfactory obesity or cognitive drugs. There is increasing evidence that histamine plays an important role in energy homeostasis. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The compounds of the present invention can readily be evaluated by using a competitive inhibition Scintillation Proximity Assay (SPA) based on a H3R binding assay using [3H] α methylhistamine as ligand. Stable cell lines, including but not limited to HEK can be transfected with cDNA coding for H3R to prepare membranes used for the binding assay. The technique is illustrated below (*Preparation of Histamine Receptor Subtype Membranes*) for the histamine receptor subtypes.

Membranes isolated as described in (*Preparation of Histamine Receptor Subtype Membranes*) are used in a [35S] GTP$_\chi$S functional assay. Binding of [35S]GTP$_\chi$S to membranes indicates agonist activity. Compounds of the invention of Formula I or Formula II are tested for their ability to inhibit binding in the presence of agonists. Alternately, the same transfected cell lines are used for a cAMP assay wherein H3R agonists inhibit forskolin-activated synthesis of cAMP. Compounds of Formula I or Formula II are tested for their ability to permit forskolin-stimulated cAMP synthesis in the presence of agonist.

Preparation of Histamine Receptor Subtype Membranes

A. Preparation H1R Membranes cDNA for the human histamine 1 receptor (H1R) is cloned into a mammalian expression vector containing the CMV promoter (pcDNA3.1(+), Invitogen) and transfected into HEK293 cells using the FuGENE Transfection Reagent (Roche Diagnostics Corporation). Transfected cells are selected using G418 (500 µ/ml). Colonies that survived selection are grown and tested for histamine binding to cells grown in 96-well dishes using a scintillation proximity assay (SPA) based radioligand binding assay. Briefly, cells, representing individual selected clones, are grown as confluent monolayers in 96-well dishes (Costar Clear Bottom Plates, #3632) by seeding wells with 25,000 cells and growing for 48 hours (37° C., 5% $CO_2$). Growth media is removed and wells are rinsed two times with PBS (minus $Ca^{2+}$ or $Mg^{2+}$). For total binding, cells are assayed in a SPA reaction containing 50 mM Tris-HCL (assay buffer), pH 7.6, 1 mg wheat germ agglutinin SPA beads (Amersham Pharmacia Biotech, #RPNQ0001), and 0.8 nM $^3$H-pyrilamine (Net-594, NEN) (total volume per well=200 µl). Astemizole (10 µM, Sigma #A6424) is added to appropriate wells to determine non-specific binding. Plates are covered with FasCal and incubated at room temperature for 120 minutes. Following incubation, plates are centrifuged at 1,000 rpm (~800 g) for 10 minutes at room temperature. Plates are counted in a Wallac Trilux 1450 Microbeta scintillation counter. Several clones are selected as positive for binding, and a single clone (H1R40) is used to prepare membranes for binding studies. Cell pellets, representing ~10 grams, are resuspended in 30 ml assay buffer, mixed by vortexing, and centrifuged (40,000 g at 4° C.) for 10 minutes. The pellet resuspension, vortexing, and centrifugation is repeated 2 more times. The final cell pellet is resuspended in 30 ml and homogenized with a Polytron Tissue Homogenizer. Protein determinations are done using the Coomassie Plus Protein Assay Reagent (Pierce). Five micrograms of protein is used per well in the SPA receptor-binding assay.

B. Preparation H2R Membranes cDNA for the human histamine 2 receptor is cloned, expressed and transfected into HEK 293 cells as described above. Histamine binding to cells is assayed by SPA described above. For total binding, cells are assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 µl). Cimetidine (10 µM, Sigma #C4522) is added to appropriate wells to determine non-specific binding.

Several clones are selected as positive for binding, and a single clone (H2R10) is used to prepare membranes for binding studies. Five micrograms of protein is used per well in the SPA receptor-binding assay.

C. Preparation of H3R Membranes cDNA for the human histamine 3 receptor is cloned and expressed as described in (A. Preparation H1R membranes), above. Transfected cells are selected using G418 (500 µ/ml), grown, and tested for histamine binding by the SPA described above. For total binding, cells are assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM ($^3$H)-n-alpha-methylhistamine (NEN, NET1027) (total volume per well=200 µl). Thioperimide is added to determine non-specific binding. Several clones are selected as positive for binding, and a single clone (H3R8) is used to prepare membranes for binding studies described above. Five micrograms of protein is used per well in the SPA receptor-binding assay.

All compounds set forth in the examples exhibit affinity for the H3 receptor greater than 1 uM. Preferred compounds of the invention exhibit affinity for the H3 receptor greater than 200 nM. Most preferred compounds of the invention exhibit affinity for the H3 receptor greater than 20 nM.

D. Preparation of GPRv53 Membranes cDNA for the human GPRv53 receptor is cloned and expressed as described in (A. Preparation H1R membranes), above. Transfected cells are selected, tested for histamine binding, and selected. HEK293 GPRv5350 cells are grown to confluency in DMEM/F12 (Gibco) supplemented with 5% FBS and 500 ug/ml G418 and washed with Delbecco's PBS (Gibco) and harvested by scraping. Whole cells are homogenized with a Polytron tissuemizer in binding buffer, 50 mM Tris pH 7.5. Cell lysates, 50 ug, are incubated in 96 well dishes with 3 nM (3H) Histamine and compounds in binding buffer for 2 hours at room temperature. Lysates are filtered through glass fiber filters (Perkin Elmer) with a Tomtec cell harvester. Filters are counted with melt-on scintillator sheets (Perkin Elmer) in a Wallac Trilux 1450 Microbeta Scintillation counter for 5 minutes.

Pharmacological Results cAMP ELISA

HEK293 H3R8 cells prepared as described above are seeded at a density of 50,000 cells/well and grown overnight in DMEM/F12 (Gibco) supplemented with 5% FBS and 500 ug/ml G418. The next day tissue culture medium is removed and replaced with 50 µl cell culture medium containing 4 mM 3-isobutyl-1-methylxanthine (Sigma) and incubated for 20 minutes at room temperature. Antagonist are added in 50 µl cell culture medium and incubated for 20 minutes at room temperature. Agonist R (−)α methylhistamine (RBI) at a dose response from $1\times10^{-10}$ to $1\times10^{-5}$ M is then added to the wells in 50 µl cell culture medium and incubated for 5 minutes at room temperature. Then 50 µl of cell culture medium containing 20 µM Forskolin (Sigma) is added to each well and incubated for 20 minutes at room temperature. Tissue culture medium is removed and cells are lysed in 0.1M HCl and cAMP is measured by ELISA (Assay Designs, Inc.).

[35S] GTP γ [S] Binding Assay

Antagonist activity of selected compounds is tested for inhibition of [35S] GTP γ [S] binding to H3R membranes in the presence of agonists. Assays are run at room temperature in 20 mM HEPES, 100 mM NaCl, 5 mM $MgCl_2$ and 10 uM GDP at pH 7.4 in a final volume of 200 ul in 96-well Costar plates. Membranes isolated from H3R8-expressing HEK293 cell line (20 µg/well) and GDP are added to each well in a volume of 50 µl assay buffer. Antagonist is then added to the wells in a volume of 501 assay buffer and incubated for 15 minutes at room temperature. Agonist R(−)alpha methylhistamine (RBI) at either a dose response from $1\times10^{-10}$ to $1\times10^{-5}$ M or fixed concentration of 100 nM are then added to the wells in a volume of 50 µl assay buffer and incubated for 5 minutes at room temperature. GTP γ [35S] is added to each well in a volume of 50 µl assay buffer at a final concentration of 200 pM, followed by the addition of 50 µl of 20 mg/ml WGA coated SPA beads (Amersham). Plates are counted in Wallac Trilux 1450 Microbeta scintillation counter for 1 minute. Compounds that inhibit more than 50% of the specific binding of radioactive ligand to the receptor are serially diluted to determine a K[i](nM). The results are given below for the indicated compound.

TABLE 2

| Example | Ki (nM) |
| --- | --- |
| [structure: 4-methoxybenzoyl pyrrolidine with pyrrolidinylmethyl substituent] | 73.6 |

TABLE 2-continued

| Example | | Ki (nM) |
|---|---|---|
| 145 | 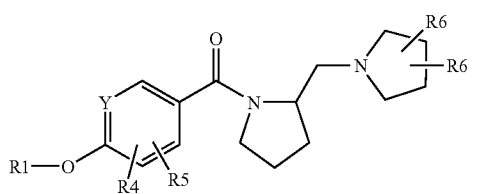 | 5 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed:
1. A compound structurally represented by Formula I

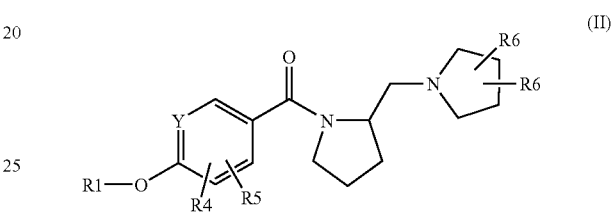

or a pharmaceutically acceptable salt thereof wherein:
Y independently represents carbon or nitrogen,
R1 is independently
—($C_1$-$C_7$) alkyl (optionally substituted with 1 to 4 halogens, or wherein R1 is —$CH_3$, then optionally substituted with 1 to 3 halogens), provided that when Y is carbon, then R1 is not —($CH_2$)$_3$—Cl,
—($C_3$-$C_8$) cycloalkyl (optionally substituted with 1 to 3 halogens),
—($C_1$-$C_7$) alkyl-O—R3, —($C_1$-$C_7$) alkyl-S(O)$_2$—($C_1$-$C_3$) alkyl,
—($C_1$-$C_7$) alkyl-C(O)—O—R3, —($C_1$-$C_7$) alkyl-S(O)$_2$-phenyl(R2)(R3)(R4),
—($C_1$-$C_7$) alkyl-S—($C_1$-$C_7$) alkyl, —($C_1$-$C_7$) alkyl-($C_3$-$C_8$) cycloalkyl,
—($C_1$-$C_7$) alkyl-O-phenyl(R2)(R3)(R4),
—($C_2$-$C_7$) alkyl-phenyl(R2)(R3)(R4), —($C_2$-$C_7$) alkenyl,
—($C_3$-$C_8$) cycloalkenyl, —($C_2$-$C_7$) alkenyl-O—R3,
—($C_2$-$C_7$) alkenyl-S(O)$_2$—($C_1$-$C_3$) alkyl, —($C_2$-$C_7$) alkenyl-C(O)—O—R3,
—($C_2$-$C_7$) alkenyl-S(O)$_2$-phenyl(R2)(R3)(R4), —($C_2$-$C_7$) alkenyl-S—($C_1$-$C_7$) alkyl, —($C_2$-$C_7$) alkenyl-($C_3$-$C_8$) cycloalkyl,
—($C_2$-$C_7$) alkenyl-O-phenyl(R2)(R3)(R4),
—($C_2$-$C_7$) alkenyl-phenyl(R2)(R3)(R4), or -phenyl optionally substituted once or twice with R2, and independently optionally substituted once or twice with R3;
R2 is independently at each occurrence
—H, -halogen, —($C_1$-$C_7$) alkyl (optionally substituted with 1 to 3 halogens),
—C(O)R7, —C(O)OR7, —C(O)($C_3$-$C_8$)cycloalkyl,
—OCF$_3$, —OR7, —SR7, —SO$_2$R7, —SO$_2$CF$_3$, or —S(O)R7;

R3 is independently at each occurrence
—H, or —($C_1$-$C_4$) alkyl (optionally substituted with 1 to 3 halogens);
R4 and R5 are independently at each occurrence
—H, -halogen, —($C_1$-$C_3$) (alkyl optionally substituted with 1 to 3 halogens), or
—OR3, provided that when Y is nitrogen, then R4 or R5 are not attached to Y;
R6 is independently at each occurrence
—H, -halogen, —CF$_3$, —($C_1$-$C_3$) alkyl (optionally substituted with 1 to 3 halogens), or —OR3; and
R7 is independently at each occurrence
—H, —($C_1$-$C_7$) alkyl, or —($C_2$-$C_7$) alkenyl (optionally substituted with 1 to 3 halogens).

2. A pharmaceutical composition comprising a compound of Formula (II), (II)

or a pharmaceutically acceptable salt thereof, and a pharmaceutically acceptable carrier, wherein:
Y independently represents carbon or nitrogen,
R1 is independently;
—H, —($C_1$-$C_7$) alkyl, —($C_3$-$C_8$) cycloalkyl, —($C_1$-$C_7$) alkyl-O—R3,
—($C_1$-$C_7$) alkyl-S(O)$_2$—($C_1$-$C_3$) alkyl, —($C_1$-$C_7$) alkyl-C(O)—O—R3,
—($C_1$-$C_7$) alkyl-S(O)$_2$-phenyl(R2)(R3)(R4), —($C_1$-$C_7$) alkyl-S—($C_1$-$C_7$) alkyl,
—($C_1$-$C_7$) alkyl-($C_3$-$C_8$) cycloalkyl, —($C_1$-$C_7$) alkyl-O-phenyl(R2)(R3)(R4),
—($C_2$-$C_7$) alkyl-phenyl(R2)(R3)(R4), —($C_2$-$C_7$) alkenyl,
—($C_3$-$C_8$) cycloalkenyl,
—($C_2$-$C_7$) alkenyl-O—R3, —($C_2$-$C_7$) alkenyl-S(O)$_2$—($C_1$-$C_3$) alkyl,
—($C_2$-$C_7$) alkenyl-C(O)—O—R3, —($C_2$-$C_7$) alkenyl-S(O)$_2$-phenyl(R2)(R3)(R4),
—($C_2$-$C_7$) alkenyl-S—($C_1$-$C_7$) alkyl, —($C_2$-$C_7$) alkenyl-($C_3$-$C_8$) cycloalkyl,
—($C_2$-$C_7$) alkenyl-O-phenyl(R2)(R3)(R4), —($C_2$-$C_7$) alkenyl-phenyl(R2)(R3)(R4), or -phenyl optionally substituted once with R2, and independently optionally substituted once or twice with R3;
R2 is independently at each occurrence
—H, -halogen, —($C_1$-$C_7$) alkyl, —C(O)R7, —C(O)OR7, —C(O)($C_3$-$C_8$)cycloalkyl,
—OCF$_3$, —OR7, —SR7, —SO$_2$R7, —SO$_2$CF$_3$, or —S(O)R7;
R3 is independently at each occurrence
—H, or —($C_1$-$C_3$) alkyl;
R4 and R5 are independently at each occurrence
—H, -halogen, —($C_1$-$C_3$)alkyl, or —OR3,
provided that when Y is nitrogen, then R4 or R5 are not attached to Y;
R6 is independently at each occurrence
—H, -halogen, —CF$_3$, —($C_1$-$C_3$) alkyl, or —OR3;
R7 is independently at each occurrence
—H, —($C_1$-$C_7$) alkyl, or —($C_2$-$C_7$) alkenyl.

3. The compound or salt of claim 1 wherein Y is carbon.
4. The compound or salt of claim 1 wherein Y is nitrogen.
5. The compound or salt of claim 3 wherein R1 is —($C_3$-$C_8$) cycloalkyl, —($C_1$-$C_7$) alkyl-O—R3, —($C_1$-$C_7$) alkyl-S(O)$_2$—($C_1$-$C_3$) alkyl, —($C_1$-$C_7$)alkyl-C(O)—O—R3, —($C_1$-$C_7$) alkyl-S—($C_1$-$C_7$) alkyl, —($C_1$-$C_7$) alkyl-($C_3$-$C_8$) cycloalkyl, or —($C_1$-$C_7$) alkyl, provided that when Y is carbon, then R1 is not —(CH$_2$)$_3$—Cl.
6. The compound or salt of claim 3 wherein R1 is —($C_1$-$C_7$) alkyl-O-phenyl(R2)(R3)(R4), —($C_2$-$C_7$) alkyl-phenyl(R2)(R3)(R4), or —($C_1$-$C_7$) alkyl-S(O)$_2$-phenyl(R2)(R3)(R4).
7. The compound or salt of claim 3 wherein R1 is —($C_2$-$C_7$) alkenyl, —($C_3$-$C_8$) cycloalkenyl, —($C_2$-$C_7$) alkenyl-O—R3, —($C_2$-$C_7$) alkenyl-S(O)$_2$—($C_1$-$C_3$) alkyl, —($C_2$-$C_7$) alkenyl-C(O)—O—R3, —($C_2$-$C_7$) alkenyl-S—($C_1$-$C_7$) alkyl, or —($C_2$-$C_7$) alkenyl-($C_3$-$C_8$) cycloalkyl.
8. The compound or salt of claim 3 wherein R1 is —($C_2$-$C_7$) alkenyl-O-phenyl(R2)(R3)(R4), —($C_2$-$C_7$) alkenyl-phenyl(R2)(R3)(R4), or —($C_2$-$C_7$) alkenyl-S(O)$_2$-phenyl(R2)(R3)(R4).
9. The compound or salt of claim 3 wherein R1 is -phenyl optionally substituted once or twice with R2, and independently optionally substituted once or twice with R3.
10. The compound or salt of claim 3 wherein R4 is halogen.
11. The compound or salt of claim 3 wherein one independent occurrence of R6 is —CH$_3$ and the second independent occurrence of R6 is H.
12. The compound of claim 1 selected from the group consisting of formulae X2 to X16, and X18 to X24, and X27 to X52:

| Formula Number | Structure |
|---|---|
| X2 | 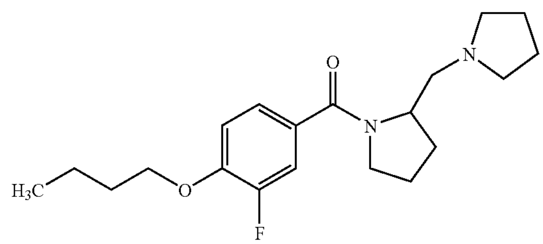 |
| X3 | 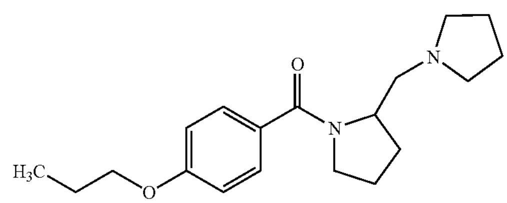 |
| X4 | 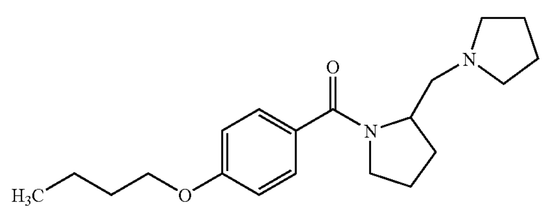 |
| X5 | 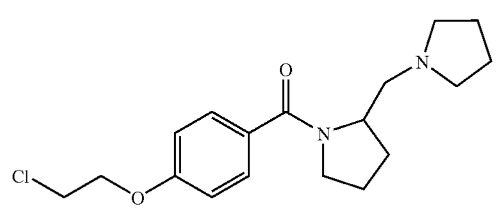 |
| X6 | 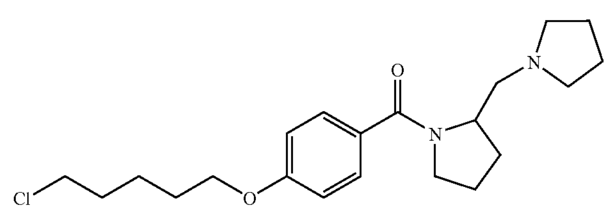 |

-continued
| Formula Number | Structure |
|---|---|
| X7 | 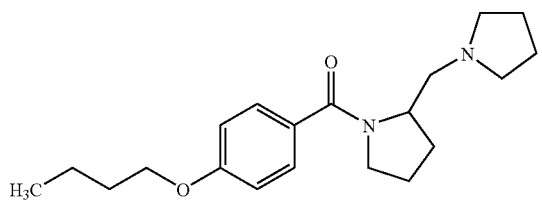 |
| X8 | 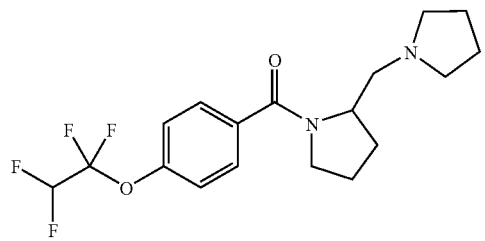 |
| X9 | 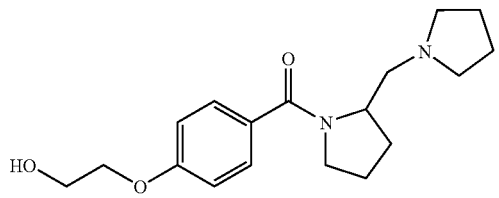 |
| X10 | 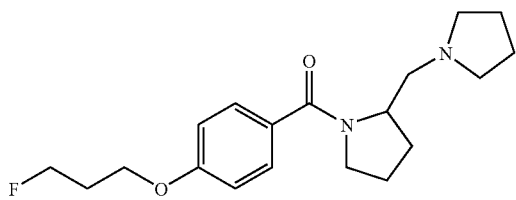 |
| X11 | 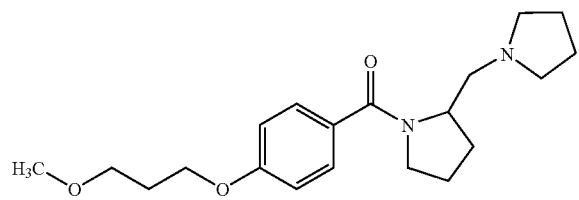 |
| X12 | 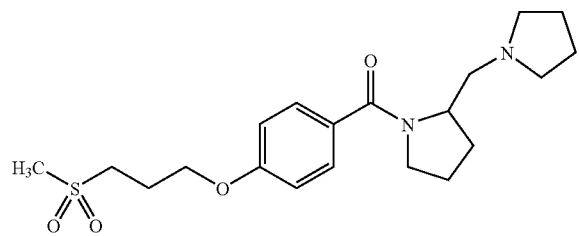 |
| X13 | 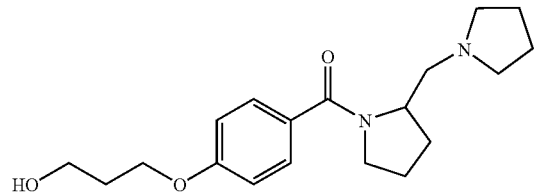 |

| Formula Number | Structure |
|---|---|
| X14 | 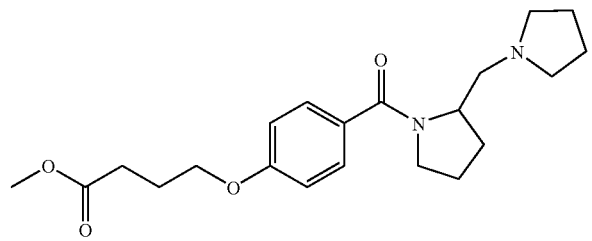 |
| X15 | 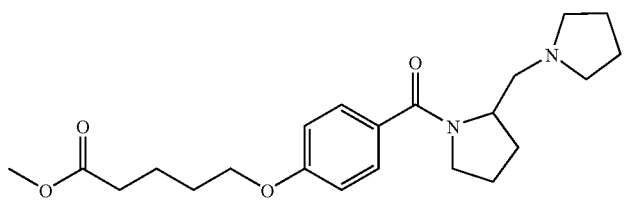 |
| X16 | 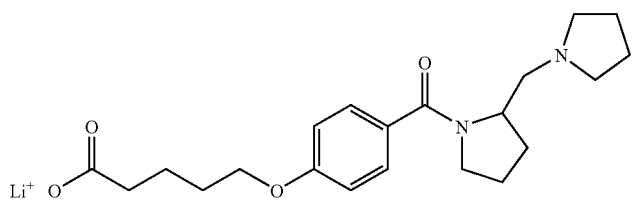 |
| X18 | 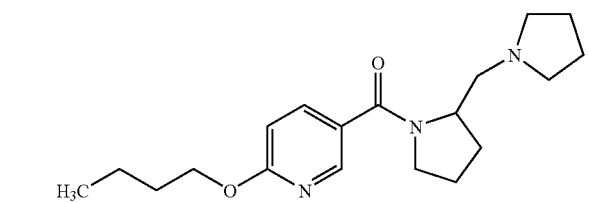 |
| X19 | 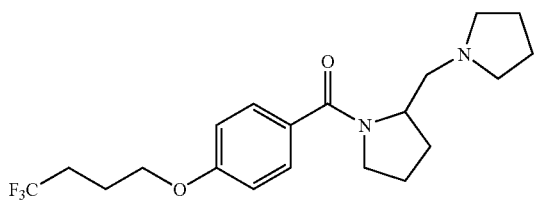 |
| X20 | 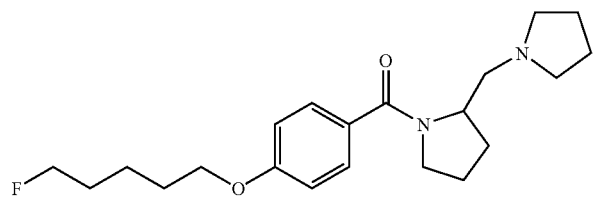 |
| X21 | 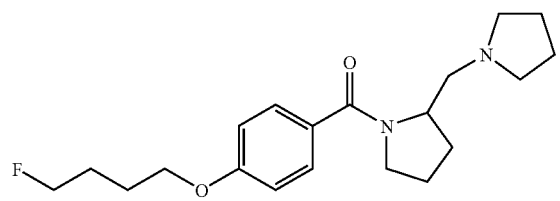 |

-continued
| Formula Number | Structure |
|---|---|
| X22 | 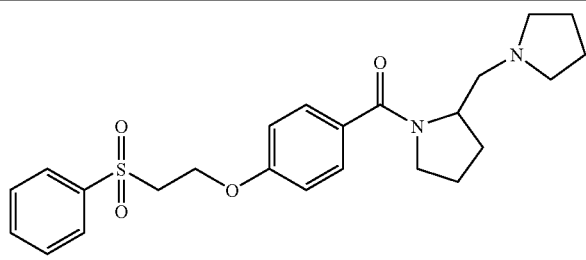 |
| X23 | 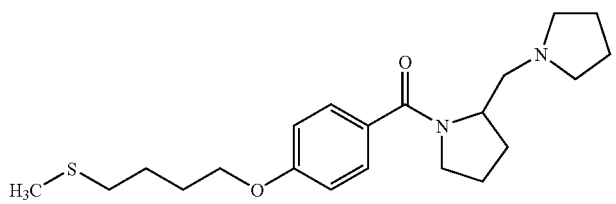 |
| X24 | 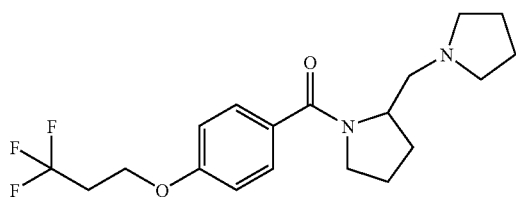 |
| X27 | 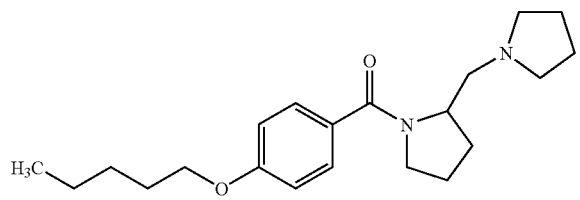 |
| X28 | 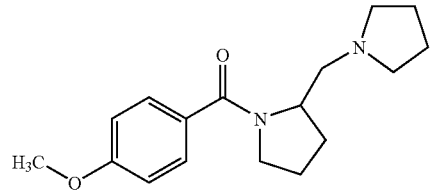 |
| X29 | 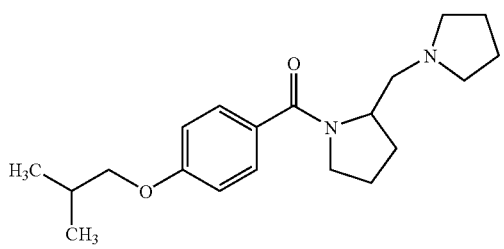 |
| X30 | 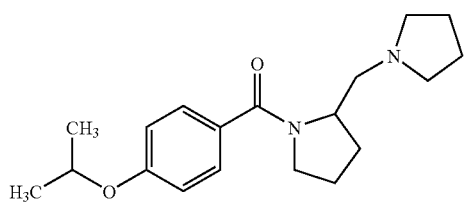 |

-continued
| Formula Number | Structure |
|---|---|
| X31 | 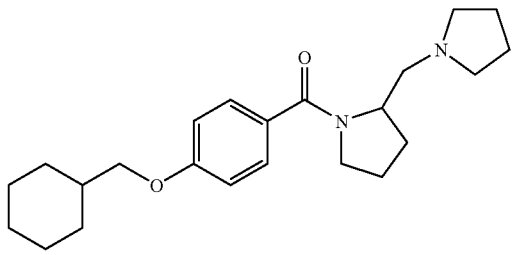 |
| X32 | 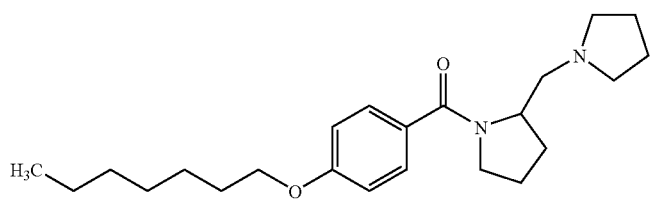 |
| X33 | 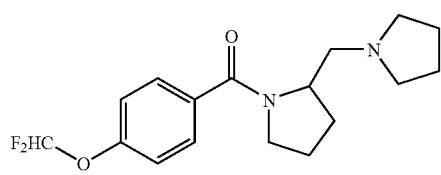 |
| X34 | 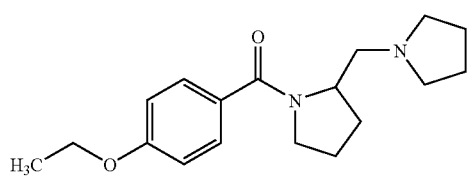 |
| X35 | 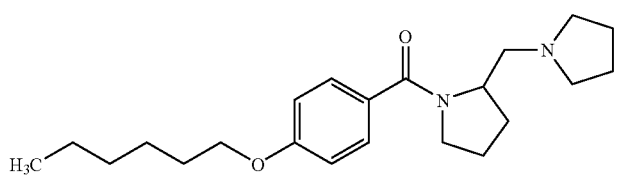 |
| X36 | 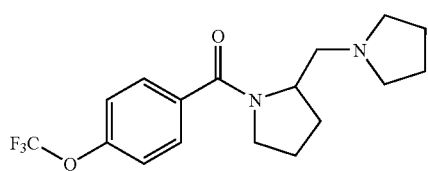 |
| X37 | 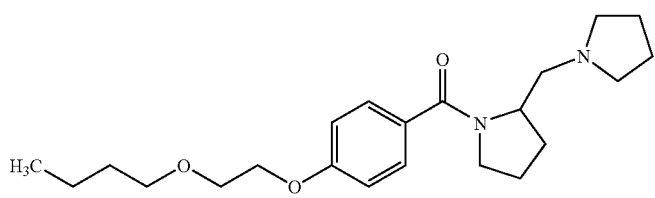 |

-continued
| Formula Number | Structure |
|---|---|
| X38 | 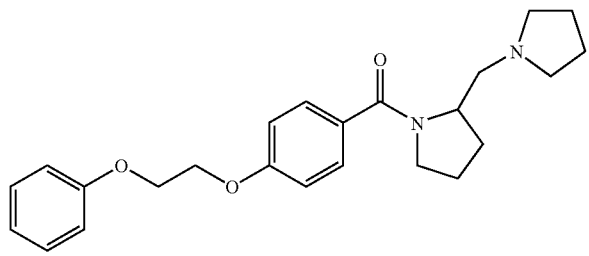 |
| X39 | 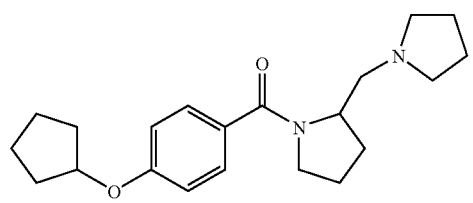 |
| X40 | 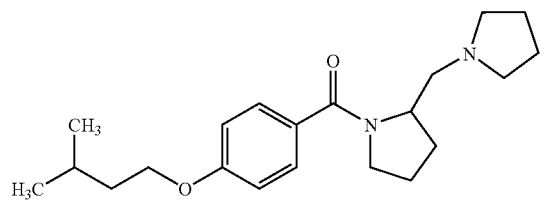 |
| X41 | 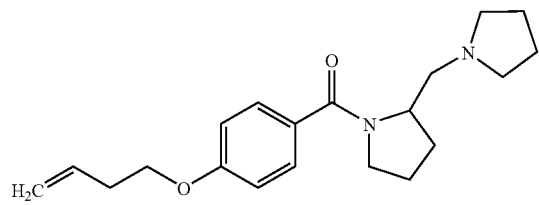 |
| X42 | 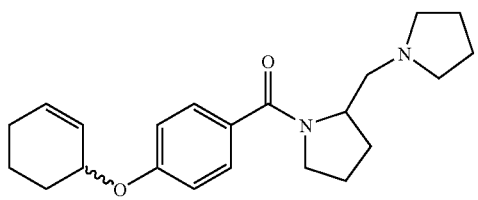 |
| X43 | 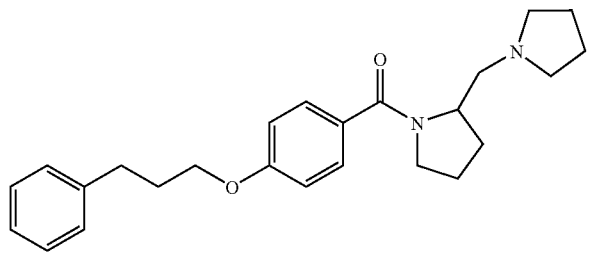 |

-continued
| Formula Number | Structure |
|---|---|
| X44 | 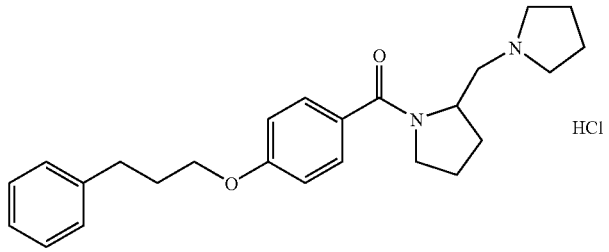 HCl |
| X45 | 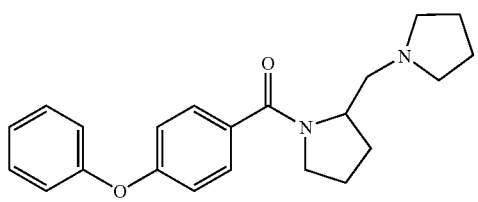 |
| X46 | 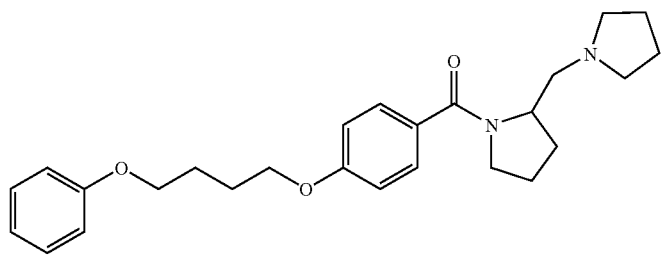 |
| X47 | 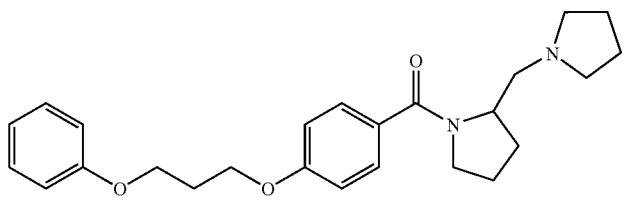 |
| X48 | 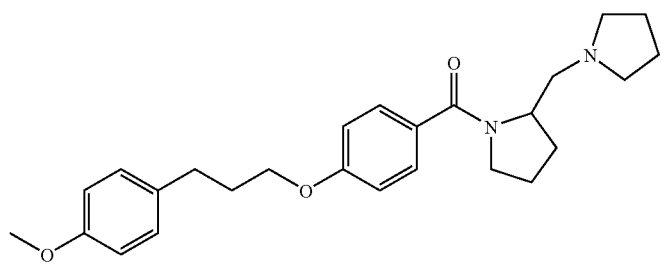 |
| X49 | 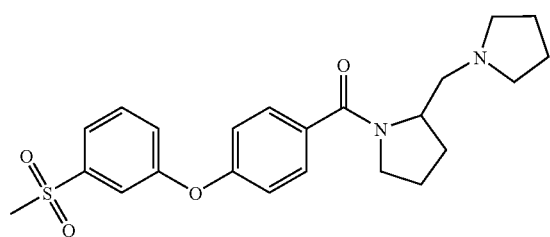 |

| Formula Number | Structure |
|---|---|
| X50 | 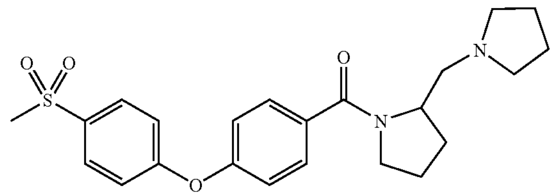 |
| X51 | 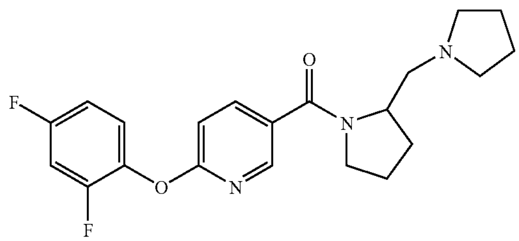 |
| X52 | | or a pharmaceutically acceptable salt thereof.

13. The compound of claim 1, selected from the group consisting of:
   S-(4-Butoxy-3-fluoro-phenyl)-(2-pyrrolidin-1-ylmethyl-pyrrolidin-1-yl)-methanone;
   (4-Propoxy-phenyl)-(2-(S)-pyrrolidin-1-ylmethyl-pyrrolidin-1-yl)-methanone;
   (4-Butoxy-phenyl)-(2-(S)-pyrrolidin-1-ylmethyl-pyrrolidin-1-yl)-methanone;
   [4-(2-Chloro-ethoxy)-phenyl]-(2-(S)-pyrrolidin-1-ylmethyl-pyrrolidin-1-yl)-methanone;
   [4-(5-Chloro-pentyloxy)-phenyl]-(2-(S)-pyrrolidin-1-ylmethyl-pyrrolidin-1-yl)-methanone;
   (4-Butoxy-phenyl)-(2-(R)-pyrrolidin-1-ylmethyl-pyrrolidin-1-yl)-methanone;
   (S)-(2-Pyrrolidin-1-ylmethyl-pyrrolidin-1-yl)-[4-(1,1,2,2-tetrafluoro-ethoxy)-phenyl]-methanone;
   [4-(2-Hydroxy-ethoxy)-phenyl]-(2-(S)-pyrrolidin-1-ylmethyl-pyrrolidin-1-yl)-methanone;
   [4-(3-Fluoro-propoxy)-phenyl]-(2-(S)-pyrrolidin-1-ylmethyl-pyrrolidin-1-yl)-methanone;
   [4-(3-Methoxy-propoxy)-phenyl]-(2-(S)-pyrrolidin-1-ylmethyl-pyrrolidin-1-yl)-methanone;
   [4-(3-Methanesulfonyl-propoxy)-phenyl]-(2-(S)-pyrrolidin-1-ylmethyl-pyrrolidin-1-yl)-methanone;
   [4-(3-Hydroxy-propoxy)-phenyl]-(2-(S)-pyrrolidin-1-ylmethyl-pyrrolidin-1-yl)-methanone;
   4-[4-(S)(+)-(2-Pyrrolidin-1-ylmethyl-pyrrolidine-1-carbonyl)-phenoxy]-butyric acid methyl ester;
   5-[4-(S)(+)-(2-Pyrrolidin-1-ylmethyl-pyrrolidine-1-carbonyl)-phenoxy]-pentanoic acid methyl ester;
   5-[4-(S)(+)-(2-Pyrrolidin-1-ylmethyl-pyrrolidine-1-carbonyl)-phenoxy]-pentanoic acid;
   (6-Butoxy-pyridin-3-yl)-(S)(+)-(2-pyrrolidin-1-ylmethyl-pyrrolidin-1-yl)-methanone;
   (2-(S)-Pyrrolidin-1-ylmethyl-pyrrolidin-1-yl)-[4-(4,4,4-trifluoro-butoxy)-phenyl]-methanone;
   [4-(5-Fluoro-pentyloxy)-phenyl]-(2-(S)-pyrrolidin-1-yl-methyl-pyrrolidin-1-yl)-methanone;
   [4-(4-Fluoro-butoxy)-phenyl]-(2-(S)-pyrrolidin-1-ylmethyl-pyrrolidin-1-yl)-methanone;
   [4-(2-Benzenesulfonyl-ethoxy)-phenyl]-(2-(S)-pyrrolidin-1-ylmethyl-pyrrolidin-1-yl)-methanone;
   [4-(4-Methylsulfanyl-butoxy)-phenyl]-(2-(S)-pyrrolidin-1-ylmethyl-pyrrolidin-1-yl)-methanone;
   (2-(S)-Pyrrolidin-1-ylmethyl-pyrrolidin-1-yl)-[4-(3,3,3-trifluoro-propoxy)-phenyl]-methanone;
   (4-Pentyloxy-phenyl)-(2-(S)-pyrrolidin-1-ylmethyl-pyrrolidin-1-yl)-methanone;
   5-Methoxy-2-methylene-1-(2-(S)-pyrrolidin-1-ylmethyl-pyrrolidin-1-yl)-pent-3-en-1-one;
   (4-Isobutoxy-phenyl)-(2-(S)-pyrrolidin-1-ylmethyl-pyrrolidin-1-yl)-methanone;
   (4-Isopropoxy-phenyl)-(2-(S)-pyrrolidin-1-ylmethyl-pyrrolidin-1-yl)-methanone;
   (4-Cyclohexylmethoxy-phenyl)-(2-(S)-pyrrolidin-1-ylmethyl-pyrrolidin-1-yl)-methanone;
   (4-Heptyloxy-phenyl)-(2-(S)-pyrrolidin-1-ylmethyl-pyrrolidin-1-yl)-methanone;
   (4-Difluoromethoxy-phenyl)-(2-(S)-pyrrolidin-1-ylmethyl-pyrrolidin-1-yl)-methanone;
   (4-Ethoxy-phenyl)-(2-(S)-pyrrolidin-1-ylmethyl-pyrrolidin-1-yl)-methanone;
   (4-Hexyloxy-phenyl)-(2-(S)-pyrrolidin-1-ylmethyl-pyrrolidin-1-yl)-methanone;
   (S)-(2-Pyrrolidin-1-ylmethyl-pyrrolidin-1-yl)-(4-trifluoromethoxy-phenyl)-methanone;
   [4-(2-Butoxy-ethoxy)-phenyl]-(2-(S)-pyrrolidin-1-ylmethyl-pyrrolidin-1-yl)-methanone;

[4-(2-Phenoxy-ethoxy)-phenyl]-(2-(S)-pyrrolidin-1-ylmethyl-pyrrolidin-1-yl)-methanone;
(4-Cyclopentyloxy-phenyl)-(2-(S)-pyrrolidin-1-ylmethyl-pyrrolidin-1-yl)-methanone;
[4-(3-Methyl-butoxy)-phenyl]-(2-(S)-pyrrolidin-1-ylmethyl-pyrrolidin-1-yl)-methanone;
(4-But-3-enyloxy-phenyl)-(2-(S)-pyrrolidin-1-ylmethyl-pyrrolidin-1-yl)-methanone;
[4-(Cyclohex-2-enyloxy)-phenyl]-(2-(S)-pyrrolidin-1-ylmethyl-pyrrolidin-1-yl)-methanone;
[4-(3-Phenyl-propoxy)-phenyl]-(2-(S)-pyrrolidin-1-ylmethyl-pyrrolidin-1-yl)-methanone;
[4-(3-Phenyl-propoxy)-phenyl]-(2-(S)-pyrrolidin-1-ylmethyl-pyrrolidin-1-yl)-methanone;
(4-Phenoxy-phenyl)-(2-(S)-pyrrolidin-1-ylmethyl-pyrrolidin-1-yl)-methanone;
[4-(4-Phenoxy-butoxy)-phenyl]-(2-(S)-pyrrolidin-1-ylmethyl-pyrrolidin-1-yl)-methanone;
{4-[3-(4-Methoxy-phenyl)-propoxy]-phenyl}-(2-(S)-pyrrolidin-1-ylmethyl-pyrrolidin-1-yl)-methanone;
[4-(3-Methanesulfonyl-phenoxy)-phenyl]-(2-(S)-pyrrolidin-1-ylmethyl-pyrrolidin-1-yl)-methanone;
[4-(4-Methanesulfonyl-phenoxy)-phenyl]-(2-(S)-pyrrolidin-1-ylmethyl-pyrrolidin-1-yl)-methanone;
(S)-[6-(2,4-Difluoro-phenoxy)-pyridin-3-yl]-(2-pyrrolidin-1-ylmethyl-pyrrolidin-1-yl)-methanone; and
(S)-(2-Pyrrolidin-1-ylmethyl-pyrrolidin-1-yl)-[6-(4-trifluoromethoxy-phenoxy)-pyridin-3-yl]-methanone;
or a pharmaceutically acceptable salt thereof.

14. A pharmaceutical composition which comprises a compound or salt of claim 13 and a pharmaceutically acceptable carrier.

15. A method for treatment of obesity which comprises administering to a mammal in need of such treatment an effective amount of a compound or salt of claim 1.

16. A method for treatment of obesity which comprises administering to a mammal in need of such treatment an effective amount of a pharmaceutical composition of claim 14.

* * * * *